United States Patent
Bartizal et al.

(10) Patent No.: US 11,712,459 B2
(45) Date of Patent: Aug. 1, 2023

(54) DOSING REGIMENS FOR TREATMENT OF FUNGAL INFECTIONS

(71) Applicant: Cidara Therapeutics, Inc., San Diego, CA (US)

(72) Inventors: Kenneth Bartizal, La Jolla, CA (US); Paul Daruwala, Del Mar, CA (US); Jeffrey Brian Locke, La Jolla, CA (US); Voon Ong, San Diego, CA (US); Taylor Sandison, Encinitas, CA (US); Dirk Thye, San Diego, CA (US)

(73) Assignee: Cidara Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/084,600

(22) PCT Filed: Mar. 15, 2017

(86) PCT No.: PCT/US2017/022551
§ 371 (c)(1),
(2) Date: Sep. 13, 2018

(87) PCT Pub. No.: WO2017/161016
PCT Pub. Date: Sep. 21, 2017

(65) Prior Publication Data
US 2019/0216885 A1 Jul. 18, 2019

Related U.S. Application Data

(60) Provisional application No. 62/436,716, filed on Dec. 20, 2016, provisional application No. 62/419,076, filed on Nov. 8, 2016, provisional application No. 62/418,727, filed on Nov. 7, 2016, provisional application No. 62/415,928, filed on Nov. 1, 2016, provisional application No. 62/350,591, filed on Jun. 15, 2016, provisional application No. 62/309,211, filed on Mar. 16, 2016.

(51) Int. Cl.
| | |
|---|---|
| *A61K 38/12* | (2006.01) |
| *A61P 31/10* | (2006.01) |
| *A61K 9/00* | (2006.01) |
| *A61P 31/00* | (2006.01) |
| *G01N 33/569* | (2006.01) |

(52) U.S. Cl.
CPC .......... *A61K 38/12* (2013.01); *A61K 9/0019* (2013.01); *A61P 31/00* (2018.01); *A61P 31/10* (2018.01); *G01N 33/56961* (2013.01)

(58) Field of Classification Search
None
See application file for complete search history.

(56) References Cited

U.S. PATENT DOCUMENTS

| | | | |
|---|---|---|---|
| 4,427,660 A | 1/1984 | Schiffman et al. | |
| 5,166,135 A | 11/1992 | Schmatz | |
| 5,378,804 A | 1/1995 | Balkovec et al. | |
| 5,399,552 A | 3/1995 | Bouffard | |
| 5,514,651 A | 5/1996 | Balkovec et al. | |
| 5,516,756 A | 5/1996 | Balkovec et al. | |
| 5,541,160 A | 7/1996 | Balkovec et al. | |
| 5,652,213 A | 7/1997 | Jamison et al. | |
| 5,741,775 A | 4/1998 | Balkovec et al. | |
| 5,854,213 A | 12/1998 | Bouffard | |
| 5,948,753 A | 9/1999 | Balkovec et al. | |
| 6,030,944 A | 2/2000 | Bouffard et al. | |
| 6,069,126 A | 5/2000 | Abruzzo et al. | |
| 6,268,338 B1 | 7/2001 | Balkovec et al. | |
| 6,506,726 B1 | 1/2003 | Dobbins et al. | |
| 6,821,951 B2 | 11/2004 | Schwier et al. | |
| 7,198,796 B2 | 4/2007 | Stogniew | |
| 7,452,861 B2 | 11/2008 | Kaniga | |
| 8,722,619 B2 | 5/2014 | James, Jr. et al. | |
| 9,217,014 B2 | 12/2015 | James, Jr. et al. | |
| 9,526,835 B2 | 12/2016 | Radhakrishnan et al. | |
| 9,676,821 B2 | 6/2017 | James, Jr. et al. | |
| 10,016,479 B2 | 7/2018 | Radhakrishnan et al. | |
| 10,369,188 B2 | 8/2019 | Bartizal et al. | |
| 10,702,573 B2 | 7/2020 | Radhakrishnan et al. | |
| 10,780,144 B2 | 9/2020 | Bartizal et al. | |
| 11,197,909 B2 | 12/2021 | Bartizal et al. | |
| 2004/0180965 A1 | 9/2004 | Borgman et al. | |
| 2005/0026819 A1 | 2/2005 | Kaniga | |
| 2005/0043222 A1 | 2/2005 | Lukacs et al. | |
| 2005/0192213 A1 | 9/2005 | Milton et al. | |
| 2005/0261173 A1 | 11/2005 | Stogniew | |
| 2006/0276339 A1 | 12/2006 | Windsor et al. | |
| 2007/0231258 A1 | 10/2007 | Perakyla et al. | |
| 2009/0074859 A1 | 3/2009 | Patel | |

(Continued)

FOREIGN PATENT DOCUMENTS

| | | |
|---|---|---|
| CN | 1222082 A | 7/1999 |
| CN | 1339959 A | 3/2002 |

(Continued)

OTHER PUBLICATIONS

Barrett, "From natural products to clinically useful antifungals," Biochim Biophys Acta. 1587(2-3):224-33 (2002).
Boikov et al., "In vitro activity of the novel echinocandin CD101 at pH 7 and 4 against *Candida* spp. isolates from patients with vulvovaginal candidiasis," J Antimicrob Chemother. 72(5):1355-8 (2017).
Bouffard et al., "Synthesis and antifungal activity of novel cationic pneumocandin Bo derivatives," J Med Chem. 37(2): 222-5 (1994).
Chatterjee et al., "Draft genome of a commonly misdiagnosed multidrug resistant pathogen *Candida auris*" BMC Genomics. 16:686 (2015) (16 pages).

(Continued)

*Primary Examiner* — H. Sarah Park
(74) *Attorney, Agent, or Firm* — Clark & Elbing LLP

(57) ABSTRACT

The disclosure features pharmaceutical compositions, methods, and kits featuring dosing regimens and CD101, or a pharmaceutical acceptable salt or neutral form thereof (e.g., CD101 acetate).

4 Claims, 11 Drawing Sheets

(56) References Cited

U.S. PATENT DOCUMENTS

| | | |
|---|---|---|
| 2009/0238867 A1 | 9/2009 | Jenkins et al. |
| 2010/0009009 A1 | 1/2010 | Young et al. |
| 2010/0075302 A1 | 3/2010 | Perlin et al. |
| 2013/0011452 A1 | 1/2013 | Loupenok |
| 2013/0150451 A1 | 6/2013 | Salamone et al. |
| 2013/0244930 A1 | 9/2013 | James, Jr. et al. |
| 2015/0024997 A1 | 1/2015 | James, Jr. et al. |
| 2015/0087583 A1* | 3/2015 | Radhakrishnan ...... A61K 38/12 514/3.6 |
| 2016/0045611 A1 | 2/2016 | Hecht et al. |
| 2016/0058717 A1 | 3/2016 | Page et al. |
| 2016/0075740 A1 | 3/2016 | James, Jr. et al. |
| 2016/0213742 A1 | 7/2016 | Forrest et al. |
| 2017/0151306 A1 | 6/2017 | Radhakrishnan et al. |
| 2017/0253635 A1 | 9/2017 | James, Jr. et al. |
| 2018/0256673 A1 | 9/2018 | Balkovec et al. |
| 2019/0000917 A1 | 1/2019 | Bartizal et al. |
| 2019/0160141 A1 | 5/2019 | Radhakrishnan et al. |
| 2019/0216885 A1 | 7/2019 | Bartizal et al. |
| 2019/0307843 A1 | 10/2019 | Bartizal et al. |
| 2019/0374601 A1 | 12/2019 | Bartizal et al. |
| 2020/0268833 A1 | 8/2020 | Bartizal et al. |
| 2021/0002346 A1 | 1/2021 | Bartizal et al. |
| 2021/0128670 A1 | 5/2021 | Radhakrishnan et al. |
| 2022/0162263 A1 | 5/2022 | James, Jr. et al. |

FOREIGN PATENT DOCUMENTS

| | | |
|---|---|---|
| CN | 1355699 A | 6/2002 |
| CN | 101374502 A | 2/2009 |
| CN | 102766198 A | 11/2012 |
| CN | 103889221 A | 6/2014 |
| CN | 104507309 A | 4/2015 |
| JP | 2014-516339 A | 7/2014 |
| JP | 2015-512392 A | 4/2015 |
| WO | WO-96/08507 A1 | 3/1996 |
| WO | WO-2005/018743 A1 | 3/2005 |
| WO | WO-2008/093060 A2 | 8/2008 |
| WO | WO-2010/032011 A2 | 3/2010 |
| WO | WO-2010/128096 A1 | 11/2010 |
| WO | WO-2011/025785 A1 | 3/2011 |
| WO | WO-2011/025875 A1 | 3/2011 |
| WO | WO-2011/089214 A1 | 7/2011 |
| WO | WO-2012/119065 A2 | 9/2012 |
| WO | WO-2013/017691 A1 | 2/2013 |
| WO | WO-2013/142279 A1 | 9/2013 |
| WO | WO-2013142279 A1 * | 9/2013 |
| WO | WO-2014/113693 A1 | 7/2014 |
| WO | WO-2014/124504 A1 | 8/2014 |
| WO | WO-2015/035102 A2 | 3/2015 |
| WO | WO-2017/049102 A1 | 3/2017 |
| WO | WO-2017/049105 A1 | 3/2017 |
| WO | WO-2017/120471 A1 | 7/2017 |
| WO | WO-2017/161016 A1 | 9/2017 |
| WO | WO-2018/085200 A1 | 5/2018 |
| WO | WO-2018/102407 A1 | 6/2018 |
| WO | WO-2018/144600 A1 | 8/2018 |
| WO | WO-2018/187574 A1 | 10/2018 |
| WO | WO-2018/191692 A1 | 10/2018 |
| WO | WO-2019/014333 A1 | 1/2019 |
| WO | WO-2019/027498 A1 | 2/2019 |
| WO | WO-2019/241626 A1 | 12/2019 |

OTHER PUBLICATIONS

Crandon et al., "Bronchopulmonary disposition of intravenous voriconazole and anidulafungin given in combination to healthy adults," Antimicrob Agents Chemother. 53(12):5102-7 (2009).

Cuenca-Estrella et al., "Susceptibility of fluconazole-resistant clinical isolates of Candida spp. to echinocandin LY303366, itraconazole and amphotericin B," J Antimicrob Chemother. 46(3): 475-7 (2000).

Cushion et al., "Echinocandin treatment of Pneumocystis pneumonia in rodent models depletes cysts leaving trophic burdens that cannot transmit the infection," PLoS One. 5(1):e8524 (2010) (12 pages).

Cushion et al., "Efficacy of CD101, a novel Echinocandin, in prevention of Pneumocystis Pneumonia (PCP): thwarting the biphasic life cycle of Pneumocystis" Annual Meeting of the American Society of Hematology, Dec. 3-6, San Diego, California, Abstract 3396. Blood. 128(22) (2016) (1 page).

Cushion et al., "Prevention of Pneumocystis Pneumonia (PCP) by the novel Echinocandin, CD101," American Society for Microbiology Microbe 2016, Jun. 17, 2016 (17 pages).

Denning et al., "Infectious Disease. How to bolster the antifungal pipeline," Science. 347(6229):1414-6 (2015) (4 pages).

Denning, "Echinocandin antifungal drugs," Lancet. 362(9390):1142-51 (2003).

Espinel-Ingroff, "Comparison of in vitro activities of the new triazole SCH56592 and the echinocandins MK-0991 (L-743,872) and LY303366 against opportunistic filamentous and dimorphic fungi and yeasts," J Clin Microbiol. 36(10): 2950-6 (1998).

Fujie et al., "FR131535, a novel water-soluble echinocandin-like lipopeptide: synthesis and biological properties," Bioorg Med Chem Lett. 11(3):399-402 (2001).

Heikkilä et al., "The prevalence of onychomycosis in Finland," Br J Dermatol. 133(5):699-703 (1995).

International Preliminary Report on Patentability for International Application No. PCT/US2017/022551, dated Sep. 27, 2018 (9 pages).

International Search Report and Written Opinion for International Application No. PCT/US2017/022551, dated Jun. 12, 2017 (15 pages).

Jamison et al., "The synthesis and antifungal activity of nitrogen containing hemiaminal ethers of LY303366," J Antibiot (Tokyo). 51(2): 239-42 (1998).

Krishnan et al., "CD101, a novel echinocandin with exceptional stability properties and enhanced aqueous solubility," J Antibiot (Tokyo). 70(2):130-5 (2017).

Metzler et al., "Comparison of minimal inhibitory and mutant prevention drug concentrations of 4 fluoroquinolones against clinical isolates of methicillin-susceptible and -resistant Staphylococcus aureus," Int J Antimicrob Agents. 24(2):161-7 (2004).

Ong et al., "Preclinical Evaluation of the Stability, Safety, and Efficacy of CD101, a Novel Echinocandin," Antimicrob Agents Chemother. 60(11):6872-9 (2016).

Pfaller et al., "Activity of a long-acting echinocandin, CD101, determined using CLSI and EUCAST reference methods, against Candida and Aspergillus spp., including echinocandin- and azole-resistant isolates," J Antimicrob Chemother. 71(10):2868-73 (2016).

Pfizer Inc., "Eraxis (anidulafungin) for Injection," <http://dailymed.nlm.nih.gov/dailymed/archives/fdaDrugInfo.cfm?archiveid-4744>, revised May 2007, retrieved on Oct. 1, 2015 (21 pages).

PubChem: Substance Record for SID 144216468, available Oct. 8, 2012, retrieved Feb. 9, 2017 (5 pages).

Sandison et al., "Pharmacokinetics, Safety, and Target Attainment of Single and Multiple Doses of CD101 IV—a Novel, Once-Weekly Echinocandin," 58th Annual Meeting of the American Society of Hematology, Dec. 5-8, San Diego, California. Abstract 2197 (2016) (1 page).

Sandison et al., "Safety and Pharmacokinetics of CD101 IV, a Novel Echinocandin, in Healthy Adults," Antimicrob Agents Chemother. 61(2):e01627-16 (2017) (11 pages).

Sandison et al., "Safety and Pharmacokinetics of Multiple Doses of CD101 IV: Results From a Phase 1, Dose-Escalation Study," ASM Microbe 2016, Jun. 16-20, Boston, Massachusetts. Abstract LB-057 (2016) (1 page).

Sandison et al., "Safety and Pharmacokinetics of Single and Multiple Doses of CD101 IV: Results from Two Phase 1 Dose-Escalation Studies," 19th Immunocompromised Host Society Symposium, 14th Forum on Fungal Infection in the Clinical Practice, Nov. 13-15, Santiago, Chile (2016) (1 page).

Sandison et al., "Safety and Pharmacokinetics of Single and Multiple Doses of CD101 IV: Results from Two Phase 1 Dose-Escalation Studies," 2016 American College of Clinical Pharmacy Annual Meeting, Oct. 23-26, Hollywood, Florida. Poster 258 (2016) (1 page).

(56) References Cited

OTHER PUBLICATIONS

Strickley, "Solubilizing excipients in oral and injectable formulations," Pharm Res. 21(2):201-30 (2004).
Thye, "The safety and single-dose pharmacokinetics of CD101 IV: results from a phase 1, dose-escalation study," 26th European Congress of Clinical Microbiology and Infectious Diseases, Amsterdam, Netherlands, Apr. 9-12, 2016. Retrieved from <http://www.cidara.com/wp-content/uploads/2016/04/The-safety-and-single-dose-pharmacokinetics-of-CD101-IV-results-from-a-phase-1-dose-escalation-study.pdf> (12 pages).
Uzun et al., "In vitro activity of a new echinocandin, LY303366, compared with those of amphotericin B and fluconazole against clinical yeast isolates," Antimicrob Agents Chemother. 41(5): 1156-7 (1997).
Verweij et al., "Efficacy of LY303366 against amphotericin B-susceptible and -resistant *Aspergillus fumigatusm* a murine model of invasive aspergillosis," Antimicrob Agents Chemother. 42(4): 873-78 (1998).
Walpole et al., "The weight of nations: an estimation of adult human biomass," BMC Public Health. 12:439 (2012) (6 pages).
Zhao et al., "CD101: a novel long-acting echinocandin," Cell Microbiol. 18(9):1308-16 (2016).
Office Action and English Translation for Russian Patent Application No. 2017128118, dated Jun. 17, 2019 (8 pages).
Rodriguez et al., "The Synthesis of Water Soluble Prodrugs Analogs of Echinocandin B," Bioorg Med Chem Lett. 9(13):1863-1868 (1999).
Garcia-Effron et al., "Effect of Candida glabrata FKS1 and FKS2 mutations on echinocandin sensitivity and kinetics of 1,3-beta-D-glucan synthase: implication for the existing susceptibility breakpoint," Antimicrob Agents Chemother. 53(9):3690-3699 (2009).
"Echinocandin Dosing: An Opportunity for Improvement," Institute for Clinical Pharmacodynamics Presentation (2017) (82 pages).
"New Hope for Serious Infections," Cidara Therapeutics Corporate Presentation (2017) (39 pages).
Bader et al., "Overcoming the Resistance Hurdle: Pharmacokinetic-Pharmacodynamic Target Attainment Analyses for Rezafungin (CD101) against Candida albicans and Candida glabrata," Antimicrob Agents Chemother. 62(6):e02614-17 (2018) (9 pages).
Chandra et al., "Evaluate the Ability of CD101 to Prevent and Treat Candida albicans Biofilms and Explore its Temporal Effect by Time Lapse Photography," 8th Trends in Medical Mycology, Oct. 6-9, Belgrade, Serbia. Abstract Poster No. P057 (2017).
Cushion et al., "Novel Once-Weekly Echinocandin Rezafungin (CD101) for Prevention and Treatment of Pneumocystis Biofilms," European Society for Blood and Marrow Transplantation (EBMT) Annual Meeting, Mar. 18-21, Lisbon, Portugal, Poster, (2018) (1 page).
Notice of Reasons for Rejection for Japanese Application No. 2018-036159, dated Nov. 12, 2019 (5 pages).
Guo et al., "Synthesis and antifungal activities of glycosylated derivatives of the cyclic peptide fungicide caspofungin," ChemMedChem. 7(8):1496-503 (2012).
James et al., "Structure-Activity Relationships of a Series of Echinocandins and the Discovery of CD101, a Highly Stable and Soluble Echinocandin with Distinctive Pharmacokinetic Properties," Antimicrob Agents Chemother. 61(2):e01541-16 (2017) (8 pages).
Lakota et al., "Pharmacological Basis of CD101 Efficacy: Exposure Shape Matters," Antimicrob Agents Chemother. 61(11):e00758-17 (2017) (7 pages).
Locke et al., "Characterization of In Vitro Resistance Development to the Novel Echinocandin CD101 in *Candida* Species," Antimicrob Agents Chemother. 60(10):6100-6107 (2016).
Ong et al., "A Single-Dose, Subcutaneous (SC) Prophylaxis CD101 Administration Prevents Fungal Infection in Mouse Models of Candidiasis and Aspergillosis," ASM Microbe, Jun. 1-5, New Orleans, Louisiana, Poster 241 (2017).
Ong et al., "Antifungal Prophylaxis with CD101 in Immunosuppressed Mouse Models of Candidiasis, Aspergillosis, and Pneumocystis Pneumonia (PCP)," European Hematology Association Congress, Jun. 22-25, Madrid, Spain, Poster P645 (2017).
Ong et al., "Efficacy of CD101, a Novel Echinocandin, In Mouse Models of Aspergillosis and Azole-Resistant Disseminated Candidiasis," ASH Annual Meeting, Dec. 3-6, San Diego, California, 3400 (2016).
Ong et al., "Pharmacokinetics of the Novel Echinocandin CD101 in Multiple Animal Species," Antimicrob Agents Chemother. 61(4):e01626-16 (2017) (8 pages).
Ong et al., "Prophylactic, Single-Dose, Subcutaneous (SC) Administration of CD101 Shows Robust Efficacy in Neutropenic Mouse Models of Candidiasis and Aspergillosis," European Congress of Clinical Microbiology and Infectious Diseases, Apr. 22-25, Vienna, Austria, EP0703 (2017).
Ong et al., "Subcutaneous (SC) Injection of CD101, a Novel Echinocandin: Efficacious, Well-Tolerated and Sustained Drug Exposures," International Immunocompromised Host Society-Infocus, Nov. 13-15, Santiago, Chile, poster (2016).
Pfaller et al., "Activity of a Long-Acting Echinocandin (CD101) and Seven Comparator Antifungal Agents Tested against a Global Collection of Contemporary Invasive Fungal Isolates in the SENTRY 2014 Antifungal Surveillance Program," Antimicrob Agents Chemother. 61(3):e02045-16 (2017) (7 pages).
Pfaller et al., "CD101, a long-acting echinocandin, and comparator antifungal agents tested against a global collection of invasive fungal isolates in the SENTRY 2015 Antifungal Surveillance Program," Int Journ Antimicrob Agents. 50(3):352-358 (2017).
Sandison, "CD101: A Novel Echinocandin," Trends in Medical Mycology, Oct. 6-9, Belgrade, Serbia, presentation (2017) (16 pages).
Zimbeck et al., "FKS mutations and elevated echinocandin MIC values among Candida glabrata isolates from U.S. population-based surveillance," Antimicrob Agents Chemother. 54(12):5042-47 (2010).
Chowdhary et al., "Multidrug-resistant Candida auris: 'new kid on the block' in hospital-associated infections?" J Hosp Infect. 94(3):209-212 (2016).
Extended European Search Report for European Patent Application No. 17867743.1, dated Jun. 25, 2020 (12 pages).
GenBank Accesion No. AYN77793.1, "1,3-beta-D-glucan synthase [[Candida] auris]," <https:///www.ncbi.nlm.nih.gov/protein/AYN77793.1>, dated Oct. 16, 2018, retrieved Oct. 16, 2020 (2 pages).
Bastin et al., "Salt Selection and Optimisation Procedures for Pharmaceutical New Chemical Entities," Org Proces Res Dev. 4:427-435 (2000).
Douglas et al., "Identification of the FKS1 gene of Candida albicans as the essential target of 1,3-beta-D-glucan synthase inhibitors," Antimicrob Agents Chemother. 41(11):2471-9 (1997).
Kathuria et al., "Multidrug-Resistant Candida auris Misidentified as Candida haemulonii: Characterization by Matrix-Assisted Laser Desorption Ionization-Time of Flight Mass Spectrometry and DNA Sequencing and Its Antifungal Susceptibility Profile Variability by Vitek 2, CLSI Broth Microdilution, and Etest Method," J Clin Microbiol. 53(6):1823-30 (2015).
James et al., "Biafungin (CD101), a novel echinocandin, displays a long half-life in the chimpanzee, suggesting a once-weekly IV dosing option," 54th Interscience Conference on Antimicrobial Agents and Chemotherapy, Sep. 5-9, Washington D.C., Abstract A-694, retrieved from <http://n33px2pjph02hfyxt1xmwn4m.wpengine.netdna-cdn.com/wp-content/uploads/2014/12/A-694.-Biafungin-CD101-a-Novel-Echinocandin-Displays-a-Long-Half-life-in-the-Chimpanzee-Suggesting-a-Once-Weekly-IV-Dosing-Option.pdf> (2014) (7 pages).
Lakota et al., "Pharmacokinetic-Pharmacodynamic Target Attainment Analyses to Support the Selection of Extended-Interval CD101 Dosing Regimens," IDWeek 2016, Oct. 26-30, New Orleans, Louisiana. Poster No. 1994 (2016) (7 pages).
Lee et al., "First three reported cases of nosocomial fungemia caused by Candida auris," J Clin Microbiol. 49(9): 3139-42 (2011).
Yasuhara et al., "Pharmacokinetics for Primers," Japanese Journal of Clinical Pharmacology and Therapeutics. 41(4):155-158 (2010) (9 pages).

\* cited by examiner

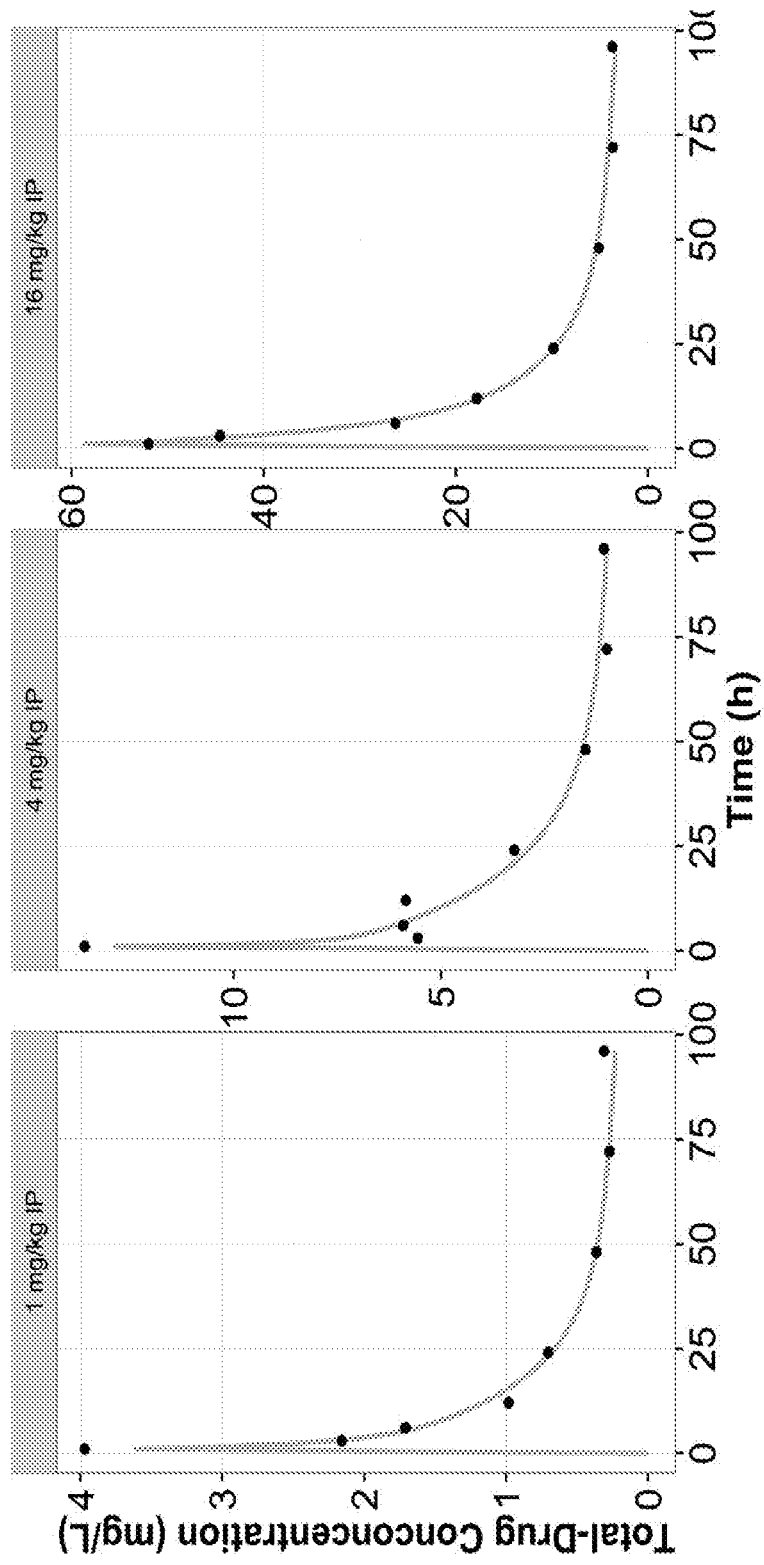
FIG. 5  Observed (solid circles) and model fitted (lines) CD101 concentrations versus time following administration of single CD101 doses

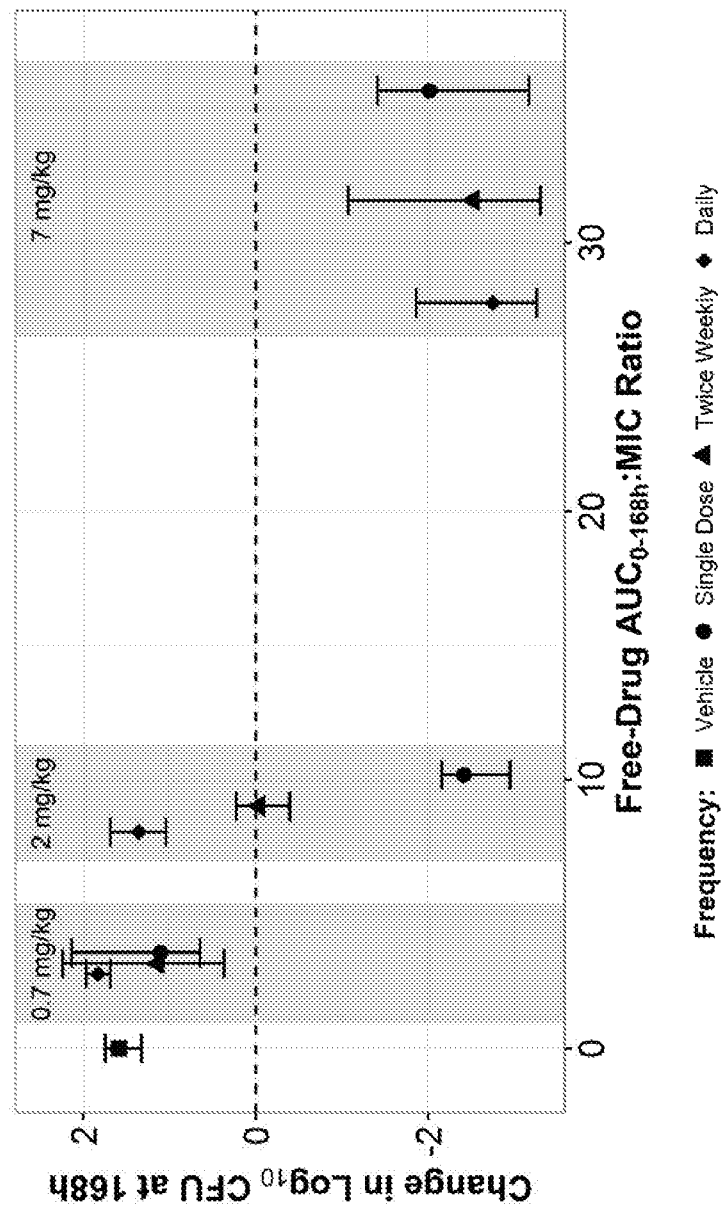
FIG. 6 Mean (solid circles) and range (error bars) change in $\log_{10}$ CFU from baseline versus $AUC_{0-168h}$:MIC ratio by fractionation schedule

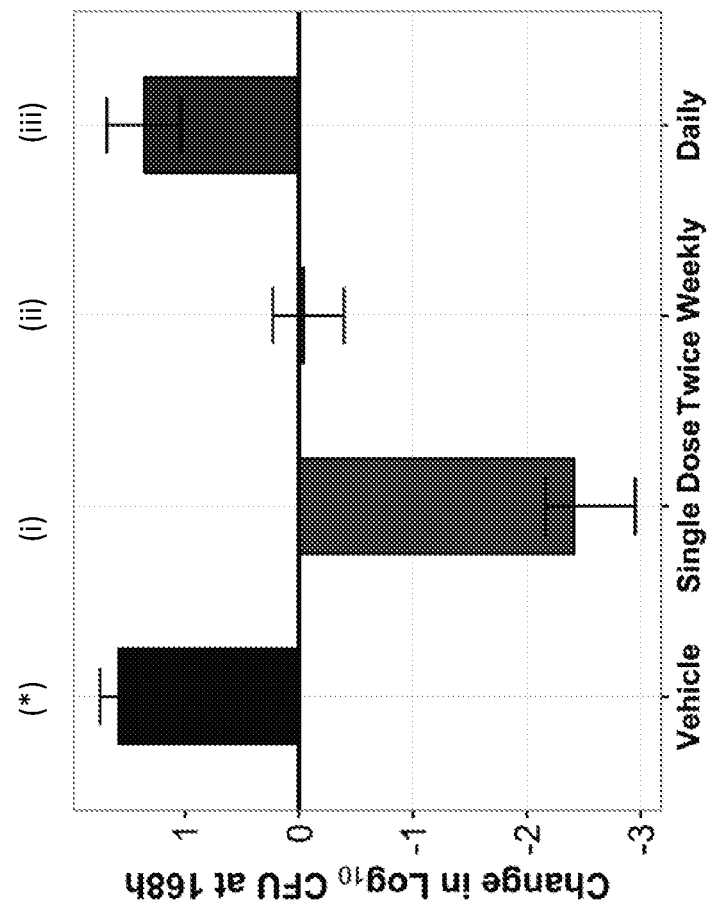
FIG. 7 Mean (bar) and range (error bars) change in $\log_{10}$ CFU from baseline allowing administration of CD101 2 mg/kg grouped by fractionation schedule
Frequency: (*) vehicle; (i) single dose; (ii) twice weekly; (iii) daily

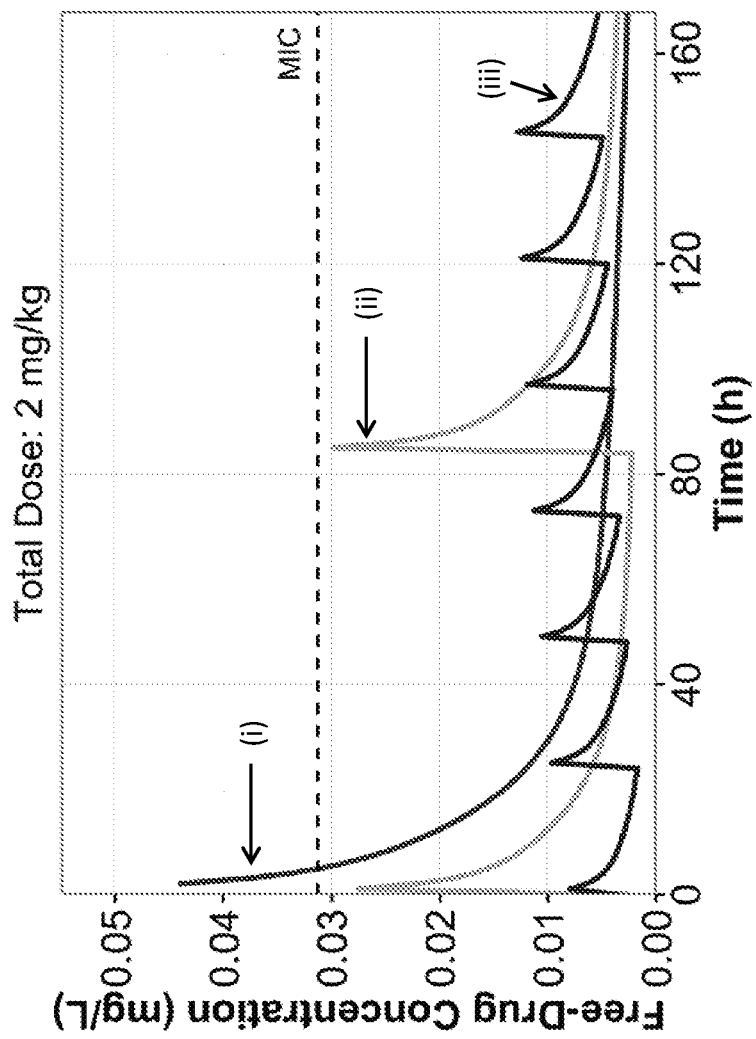
FIG. 8 Simulated free-drug concentration time profiles relative to the MIC for the fractionated CD101 2 mg/kg regimen

FIG. 10

| Organism | MRL | CD101 24h 50% | CD101 24h 100% | CD101 48h 50% | CD101 48h 100% | 5FC 48h 50% | AMB 24h 100% | AMB 48h 100% | ANID 24h 50% | CAS 24h 50% | FLU 24h 50% | FLU 48h 50% | ITRA 48h 50% | MICA 24h 50% | POSA 48h 50% | VORI 24h 50% | VORI 48h 50% |
|---|---|---|---|---|---|---|---|---|---|---|---|---|---|---|---|---|---|
| C. auris | 35364 | 0.25 | 0.25 | 0.25 | 2 | 1 | 1 | 2 | 0.125 | 0.5 | 1 | 2 | <0.063 | 2 | 0.25 | <0.063 | <0.063 |
| C. auris | 35366 | 0.25 | 0.25 | 0.25 | 1 | 0.5 | 1 | 2 | 0.125 | 0.5 | 2 | >64 | 1 | 1 | 1 | 0.5 | 2 |
| C. auris | 35367 | 0.125 | 0.5 | 0.5 | >4 | 0.5 | 1 | 2 | 0.125 | 0.5 | 16 | >64 | 1 | 1 | 0.25 | 0.25 | 2 |
| C. auris | 35368 | 0.063 | 2 | 1 | 4 | 0.5 | 4 | 4 | 0.125 | 0.5 | 32 | >64 | 1 | 2 | 0.5 | 0.5 | 0.5 |
| C. auris | 35370 | 0.125 | 1 | 0.5 | 2 | 0.5 | 4 | 4 | 0.125 | 0.5 | 32 | >64 | 1 | 1 | 0.25 | 0.5 | 0.5 |
| C. auris | 35371 | 0.25 | 1 | 1 | 2 | 0.5 | 4 | 4 | 0.125 | 0.5 | 32 | >64 | 1 | 1 | 0.5 | 1 | 2 |
| C. auris | 35372 | 0.125 | 2 | 1 | >4 | 1 | 8 | 8 | 0.25 | 0.5 | 8 | >64 | 0.5 | 1 | 0.5 | 0.5 | 1 |
| C. auris | 35373 | 0.25 | 1 | 0.5 | >4 | 0.5 | 2 | 4 | 0.25 | 1 | >64 | >64 | 0.5 | 1 | 0.5 | 0.5 | 1 |
| C. auris | 35374 | 0.25 | 2 | 0.25 | 2 | 0.5 | 2 | 4 | 0.125 | 1 | >64 | >64 | 0.5 | 1 | 1 | 0.5 | 0.5 |
| C. auris | 35375 | 0.125 | 1 | 0.25 | >4 | 0.5 | 2 | 4 | 0.125 | 0.25 | 1 | >64 | 0.5 | 1 | 0.5 | 0.5 | 2 |
| C. auris | 35376 | 0.031 | 2 | 0.125 | >4 | 0.5 | 0.5 | 4 | 0.125 | 1 | 1 | >64 | 0.5 | 1 | 0.25 | 1 | 1 |
| C. auris | 35377 | 0.063 | 4 | 0.063 | >4 | 1 | 2 | 8 | 0.125 | 0.5 | 2 | >64 | 0.5 | 2 | 0.25 | 0.5 | 0.5 |
| C. auris | 35378 | 0.125 | 0.5 | 0.25 | 2 | 0.5 | 4 | 4 | 0.125 | 1 | >64 | >64 | 0.5 | 1 | 0.25 | 0.5 | 0.5 |
| C. auris | 35379 | 0.031 | 0.5 | 0.031 | >4 | 1 | 2 | 8 | 0.25 | 1 | >64 | >64 | 1 | 2 | 1 | 1 | 2 |
| | Range | 0.031-0.25 | 0.25-4 | 0.031-1 | 0.5->4 | 0.5-1 | 0.5-8 | 2-8 | 0.125-0.25 | 0.25-1 | 1->64 | 2->64 | <0.063-1 | 1-2 | 0.25-1 | <0.063-1 | <0.063-2 |
| | MIC$_{50}$ | 0.125 | 1 | 0.25 | 2 | 0.5 | 2 | 4 | 0.125 | 0.5 | 8 | >64 | 0.5 | 1 | 0.25 | 0.5 | 1 |
| | MIC$_{90}$ | 0.25 | 2 | 0.5 | >4 | 1 | 4 | 8 | 0.25 | 1 | >64 | >64 | 1 | 2 | 1 | 1 | 2 |

MIC (μg/mL)

DOSING REGIMENS FOR TREATMENT OF FUNGAL INFECTIONS

BACKGROUND

The disclosure relates to the field of treatment of fungal infections.

Systemic infections caused by *Candida* are serious and life-threatening infections that represent a significant public health issue, particularly in highly vulnerable patient populations such as the elderly, post-surgical, critically ill, and other hospitalized patients with serious medical conditions. Because of increasing resistance to existing antifungal drugs, there is an urgent need to develop new and more effective antifungal agents to treat these serious infections. The Centers for Disease Control and Prevention recently warned that fluconazole-resistant *Candida* have the potential to pose a serious threat to public health. However, since 2007, no new antifungal agents have been approved for treatment of candidemia. Thus there is a need for new treatments of *Candida* and other fungal infections.

SUMMARY OF THE DISCLOSURE

We have discovered dosing regimens for administration of CD101, a broad-spectrum antifungal agent with excellent activity against wild-type and azole- and echinocandin-resistant strains of *Candida* spp.

In a first aspect is a method of treating a fungal infection in a subject. This method consists of the steps of (a) intravenously administering a first dose of 400±25 mg of CD101 in salt or neutral form; (b) intravenously administering a second dose of 200±25 mg of CD101 in salt or neutral form, and (c) optionally intravenously administering a third dose of 200±25 mg of CD101 in salt or neutral form. In this method, the first dose is administered on day 1, the second dose is administered between days 7 and 9 (e.g., on day 8), and the third dose, if administered, is administered between day 14 and day 16 (e.g., on day 15).

In a second aspect is a method of treating a fungal infection in a subject by (a) intravenously administering a first dose including 400±25 mg of CD101 in salt or neutral form, (b) intravenously administering a second dose including 200±25 mg of CD101 in salt or neutral form, (c) intravenously administering a third dose including 200±25 mg of CD101 in salt or neutral form, and (d) optionally intravenously administering a fourth dose including 200±25 mg of CD101 in salt or neutral form. In this method, the first dose is administered on day 1, the second dose is administered between days 7 and 9 (e.g., on day 8), the third dose is administered between day 14 and day 16 (e.g., on day 15), and the fourth dose, if administered, is administered between day 21 and 23 (e.g., on day 22).

In some embodiments of the second aspect, the method further includes optionally intravenously administering a fifth dose including 200±25 mg of CD101 in salt or neutral form, wherein the fifth dose, if administered, is administered between day 28 and day 30 (e.g., on day 29). In further embodiments, the method further includes optionally intravenously administering a sixth dose including 200±25 mg of CD101 in salt or neutral form, wherein the sixth dose, if administered, is administered between day 35 and day 37 (e.g., on day 36).

In some embodiments, the first dose is 400 mg of CD101 in salt or neutral form and the second and third doses are each 200 mg CD101 in salt or neutral form.

In a third aspect is a method of treating a fungal infection in a subject. This method consists of the steps of (a) intravenously administering a first dose of 400±25 mg of CD101 in salt or neutral form; (b) intravenously administering a second dose of 400±25 mg of CD101 in salt or neutral form, and (c) optionally intravenously administering a third dose of 400±25 mg of CD101 in salt or neutral form. In this method, the first dose is administered on day 1, the second dose is administered between days 7 and 9 (e.g., on day 8), and the third dose, if administered, is administered between day 14 and day 16 (e.g., on day 15).

In a fourth aspect is a method of treating a fungal infection in a subject by (a) intravenously administering a first dose including 400±25 mg of CD101 in salt or neutral form, (b) intravenously administering a second dose including 400±25 mg of CD101 in salt or neutral form, (c) intravenously administering a third dose including 400±25 mg of CD101 in salt or neutral form, and (d) optionally intravenously administering a fourth dose including 400±25 mg of CD101 in salt or neutral form. In this method, the first dose is administered on day 1, the second dose is administered between days 7 and 9 (e.g., on day 8), the third dose is administered between day 14 and day 16 (e.g., on day 15), and the fourth dose, if administered, is administered between day 21 and day 23 (e.g., on day 22).

In some embodiments of the fourth aspect, the method further includes optionally intravenously administering a fifth dose including 400±25 mg of CD101 in salt or neutral form, wherein the fifth dose, if administered, is administered between day 28 and day 30 (e.g., on day 29). In further embodiments, the method further includes optionally intravenously administering a sixth dose including 400±25 mg of CD101 in salt or neutral form, wherein the sixth dose, if administered, is administered on between day 35 and day 37 (e.g., on day 36).

In some embodiments, the first, second, and third doses are each 400 mg CD101 or salt or neutral form thereof.

In some embodiments, CD101 in salt or neutral form is administered until mycological eradication, improvement in clinical signs and symptoms, and/or clinical cure is achieved as determined by a standard test known in the art. In some embodiments, mycological eradication is defined as one negative blood culture. In some embodiments, mycological eradication is defined as two negative blood cultures drawn at ≥12 hours apart without intervening positive blood cultures and no change of antifungal therapy for the fungal infection.

In some embodiments, CD101 in salt or neutral form is administered until the subject is free of symptoms of the fungal infection, such as fever, cough, shortness of breath, weight loss, night sweats, tachycardia, tachypnea, hypotension, and/or hypothermia, as determined by a physician.

In some embodiments of the first and aspects, the third dose including 200±25 mg (e.g., 200 mg) of CD101 in salt or neutral form is administered if on day 15 mycological eradication and/or clinical cure has not been achieved in the subject. In other embodiments of the first and second aspects, the third dose including 200±25 mg (e.g., 200 mg) of CD101 in salt or neutral form is not administered if mycological eradication and/or clinical cure has been achieved in the subject. In other embodiments of the first and second aspects, the third dose including 200±25 mg (e.g., 200 mg) of CD101 in salt or neutral form is administered if on day 15 the subject displays symptoms of a fungal infection.

In some embodiments of the third and fourth aspects, the third dose including 400±25 mg (e.g., 400 mg) of CD101 in salt or neutral form is administered if on day 15 mycological eradication and/or clinical cure is not achieved in the subject. In other embodiments of the third and fourth aspects, the third dose including 400±25 mg (e.g., 400 mg) of CD101 in salt or neutral form is not administered if on day 15 mycological eradication and/or clinical cure is achieved in the subject. In other embodiments of the third and fourth aspects, the third dose including 400±25 mg (e.g., 400 mg) of CD101 in salt or neutral form is administered if on day 15 the subject displays symptoms of a fungal infection.

In some embodiments, mycological eradication is determined by one negative blood culture. In some embodiments, mycological eradication is determined by two negative blood cultures drawn at ≥12 hours apart without intervening positive blood cultures.

In some embodiments, symptoms of fungal infections comprises fever, cough, shortness of breath, weight loss, night sweats, tachycardia, tachypnea, hypotension, and/or hypothermia.

In other embodiments of the first to fourth aspects, the fungal infection is a *Candida* infection (e.g., an infection of *Candida albicans, C. glabrata, C. dubliniensis, C. krusei, C. parapsilosis, C. tropicalis, C. orthopsilosis, C. guilliermondii, C. rugosa, C. auris, C. lusitaniae,* or other *Candida* species). *Candida* infections include candidemia, invasive candidiasis, oropharyngeal candidiasis, esophageal candidiasis, mucosal candidiasis, genital candidiasis, vulvovaginal candidiasis, gastrointestinal candidiasis, rectal candidiasis, hepatic candidiasis, renal candidiasis, pulmonary candidiasis, splenic candidiasis, otomycosis, osteomyelitis, septic arthritis, and cardiovascular candidiasis. In some embodiments, the cardiovascular candidiasis is endocarditis. In some embodiments, the mucosal candidiasis is eye candidiasis, ear candidiasis, or mouth candidiasis.

In a fifth aspect, the disclosure features a method of administering CD101 to a subject, wherein the method consists of (a) intravenously administering a first dose comprising 400±25 mg of CD101 in salt or neutral form, (b) intravenously administering a second dose comprising 200±25 mg of CD101 in salt or neutral form, and (c) optionally intravenously administering a third dose comprising 200±25 mg of CD101 in salt or neutral form, wherein the first dose is administered on day 1, the second dose is administered between day 7 and day 9 (e.g., on day 8), and the third dose, if administered, is administered between day 14 and day 16 (e.g., on day 15).

In some embodiments of the fifth aspect, the first dose is 400 mg of CD101 in salt or neutral form and the second and third doses are each 200 mg CD101 in salt or neutral form.In a sixth aspect, the disclosure features a method of administering CD101 to a subject, wherein the method consisting of (a) intravenously administering a first dose including 400±25 mg of CD101 in salt or neutral form, (b) intravenously administering a second dose including 200±25 mg of CD101 in salt or neutral form, (c) intravenously administering a third dose including 200±25 mg of CD101 in salt or neutral form, and (d) optionally intravenously administering a fourth dose including 200±25 mg of CD101 in salt or neutral form, wherein the first dose is administered on day 1, the second dose is administered between day 7 and day 9 (e.g., on day 8), the third dose is administered between day 14 and day 16 (e.g., on day 15), and the fourth dose, if administered, is administered between day 21 and day 23 (e.g., on day 22).

In some embodiments of the sixth aspect, the first dose is 400 mg of CD101 in salt or neutral form and the second, third, and fourth doses are each 200 mg CD101 in salt or neutral form.

In some embodiments of the sixth aspect, the method further includes optionally intravenously administering a fifth dose including 200±25 mg of CD101 in salt or neutral form, wherein the fifth dose, if administered, is administered between day 28 and day 30 (e.g., on day 29). In further embodiments, the method further includes optionally intravenously administering a sixth dose including 200±25 mg of CD101 in salt or neutral form, wherein the sixth dose, if administered, is administered between day 35 and day 37 (e.g., on day 36).

In a seventh aspect, the disclosure features a method of administering CD101 to a subject, wherein the method consisting of (a) intravenously administering a first dose comprising 400±25 mg of CD101 in salt or neutral form, (b) intravenously administering a second dose comprising 400±25 mg of CD101 in salt or neutral form, and (c) optionally intravenously administering a third dose comprising 400±25 mg of CD101 in salt or neutral form, wherein the first dose is administered on day 1, the second dose is administered between day 7 and day 9 (e.g., on day 8), and the third dose, if administered, is administered between day 14 and day 16 (e.g., on day 15).

In some embodiments of the seventh aspect, the first, second, and third doses are each 400 mg CD101 or salt or neutral form thereof.

In an eighth aspect, the disclosure features a method of administering CD101 to a subject, wherein the method consisting of (a) intravenously administering a first dose including 400±25 mg of CD101 in salt or neutral form, (b) intravenously administering a second dose including 400±25 mg of CD101 in salt or neutral form, (c) intravenously administering a third dose including 400±25 mg of CD101 in salt or neutral form, and (d) optionally intravenously administering a fourth dose including 400±25 mg of CD101 in salt or neutral form, wherein the first dose is administered on day 1, the second dose is administered between day 7 and day 9 (e.g., on day 8), the third dose is administered between day 14 and day 16 (e.g., on day 15), and the fourth dose, if administered, is administered between day 21 and day 23 (e.g., on day 22).

In some embodiments of the eighth aspect, the first, second, third, and fourth doses are each 400 mg CD101 or salt or neutral form thereof.

In some embodiments of the eighth aspect, the method further includes optionally intravenously administering a fifth dose including 400±25 mg of CD101 in salt or neutral form, wherein the fifth dose, if administered, is administered between day 28 and day 30 (e.g., on day 29). In further embodiments, the method further includes optionally intravenously administering a sixth dose including 400±25 mg of CD101 in salt or neutral form, wherein the sixth dose, if administered, is administered between day 35 and day 37 (e.g., on day 36).

In embodiments of any of the above aspects, CD101 in salt or neutral form is administered over a time period of 30 to 180 minutes (e.g., over 30±5 minutes, 60±5 minutes, 90±5 minutes, 120±5 minutes, 150±5 minutes, 180±5 minutes, 30±10 minutes, 60±10 minutes, 90±10 minutes, 120±10 minutes, 150±10 minutes, or 180±10 minutes).

In embodiments of any of the above aspects, CD101 in salt or neutral form is administered as an aqueous pharmaceutical composition (e.g., a pharmaceutical composition having a pH of from 4.0 to 8).

In any of the above aspects, the salt of CD101 is CD101 acetate.

In some embodiments of the methods described herein, CD101 in salt or neutral form is administered for 2-12 doses (e.g., 2-3 doses).

As used herein, the terms "intravenous administration" or "intravenously administering" refer to intravenous bolus injection or infusion of a drug to a subject.

By "an amount sufficient" is meant the amount of an additive required to increase the oral bioavailability of a drug.

By "fungal infection" is meant the invasion of a host by pathogenic fungi. For example, the infection may include the excessive growth of fungi that are normally present in or on the body of a human or growth of fungi that are not normally present in or on a human. More generally, a fungal infection can be any situation in which the presence of a fungal population(s) is damaging to a host body. Thus, a human is "suffering" from a fungal infection when an excessive amount of a fungal population is present in or on the person's body, or when the presence of a fungal population(s) is damaging the cells or other tissue of the person.

As used herein, the term "a drug-resistant fungal infection" refers to a fungal infection that is refractory to treatment with a drug, e.g., an antifungal drug. In such infections the fungus that causes the infection is resistant to treatment with one or more antifungal drugs (e.g., an antifungal drug-resistant strain of fungus (e.g., an antifungal drug-resistant strain of *Candida* spp.)). Antifungal drugs include, but are not limited to, echinocandins, polyene compounds, flucytosine, and azole compounds. Fungal infections may be caused by a fungus in the genus, e.g., *Candida* (e.g., *C. albicans, C. glabrata, and C. auris*) or *Aspergillus* (e.g., *A. fumigatus*). In some embodiments, a fungal infection may also be a dermatophyte infection.

As used herein, the term "echinocandin-resistant fungal infection" refers to a fungal infection that is refractory to treatment with an echinocandin. In such infections the fungus that causes the infection is resistant to treatment with one or more echinocandins. The one or more echinocandins are cyclic lipopeptides that inhibit the synthesis of glucan in the cell wall by inhibition of the 1,3-β-D-glucan synthase enzyme complex. The one or more echinocandins referred to in the term "echinocandin-resistant fungal infection" include micafungin, caspofungin, and anidulafungin, but does not include CD101 or salts or neutral forms thereof. Thus, using the methods of the disclosure, CD101 or a salt or neutral form thereof can be used to treat micafungin-resistant, caspofungin-resistant, and/or anidulafungin-resistant fungal infections.

As used herein, the term "polyene-resistant fungal infection" refers to a fungal infection that is refractory to treatment with a polyene compound. In such infections, the fungus that causes the infection is resistant to treatment with one or more polyene compounds. Polyene compounds are compounds that insert into fungal membranes, bind to ergosterol and structurally related sterols in the fungal membrane, and disrupt membrane structure integrity, thus causing leakage of cellular components from a fungus that causes infection. Polyene compounds typically include large lactone rings with three to eight conjugated carbon-carbon double bonds and may also contain a sugar moiety and an aromatic moiety. Examples of polyene compounds include, but are not limited to, 67-121-A, 67-121-C, amphotericin B, arenomvcin B, aurenin, aureofungin A, aureotuscin, candidin, chinin, demethoxyrapamycin, dermostatin A, dermostatin B, DJ-400-$B_1$, DJ-400-$B_2$, elizabethin, eurocidin A, eurocidin B, filipin I, filipin II, filipin III, filipin IV, fungichromin, gannibamycin, hamycin, levorin $A_2$, lienomycin, lucensomycin, mycoheptin, mycoticin A, mycoticin B, natamycin, nystatin A, nystatin $A_3$, partricin A, partricin B, perimycin A, pimaricin, polifungin B, rapamycin, rectilavendomvcin, rimocidin, roflamycoin, tetramycin A, tetramycin B, tetrin A, and tetrin B.

As used herein, the term "flucytosine-resistant fungal infection" refers to a fungal infection that is refractory to treatment with the synthetic antifungal drug flucytosine. A brand name for flucytosine is Ancobon®.

As used herein, the term "azole-resistant fungal infection" refers to a fungal infection that is refractory to treatment with an azole compound. In such infections the fungus that causes the infection is resistant to treatment with one or more azole compounds. The azole compounds referred to in the term "azole-resistant fungal infection" are antifungal compounds that contain an azole group, which is a five-membered heterocyclic ring having at least one N and one or more heteroatoms selected from N, O, or S. Antifungal azole compounds function by binding to the enzyme 14α-demethylase and disrupt, inhibit, and/or prevent its natural function. The enzyme 14α-demethylase is a cytochrome P450 enzyme that catalyzes the removal of the C-14 α-methyl group from lanosterol before lanosterol is converted to ergosterol, an essential component in the fungal cell wall. Therefore, by inhibiting 14α-demethylase, the synthesis of ergosterol is inhibited. Examples of azole compounds include, but are not limited to, VT-1161, VT-1598, fluconazole, albaconazole, bifonazole, butoconazole, clotrimazole, econazole, efinaconazole, fenticonazole, isavuconazole, isoconazole, itraconazole, ketoconazole, luliconazole, miconazole, omoconazole, oxiconazole, posaconazole, pramiconazole, ravuconazole, sertaconazole, sulconazole, terconazole, tioconazole, and voriconazole.

As used herein, the term "antifungal therapy" refers to treatment of a fungal infection using an antifungal drug. Antifungal drugs used in an antifungal therapy include, but are not limited to, echinocandins, polyene compounds, flucytosine, azole compounds, enfumafungin, and SCY-078, APX001. As described herein, an aspect of the disclosure is a method of treating a fungal infection in a subject who has failed treatment with an antifungal therapy. The antifungal drugs used in the antifungal therapy in this aspect of the disclosure do not include CD101 or a salt or neutral form thereof.

As used herein, the term "echinocandin therapy" refers to a treatment for a fungal infection using an echinocandin (such as micafungin, caspofungin, and anidulafungin, but not a salt of Compound 1, or a neutral form thereof). As described herein, in some embodiments, a subject who has failed treatment with an echinocandin therapy may be administered a salt of Compound 1, or a neutral form thereof, to treat a fungal infection. In some embodiments, a subject having a fungal infection may be administered CD101 or a salt or neutral form thereof if the fungal infection has failed treatment with an echinocandin therapy.

As used herein, the term "polyene therapy" refers to a treatment for a fungal infection using a polyene compound. As described herein, in some embodiments, a subject who has failed treatment with a polyene therapy may be administered CD101 or a salt or neutral form thereof to treat a fungal infection. In some embodiments, a subject having a fungal infection may be administered CD101 or a salt or neutral form thereof if the fungal infection has failed treatment with a polyene therapy.

As used herein, the term "azole therapy" refers to a treatment for a fungal infection using an azole compound. Examples of antifungal azole compounds include, but are not limited to, VT-1161, VT-1598, fluconazole, albacona- As used herein, the term "CD101 salt" refers to a salt of the compound of Formula 1. CD101 has a structure (below) in which the tertiary ammonium ion positive charge of CD101 is balanced with a negative counterion (e.g., an acetate) in its salt form.

(Formula 1)

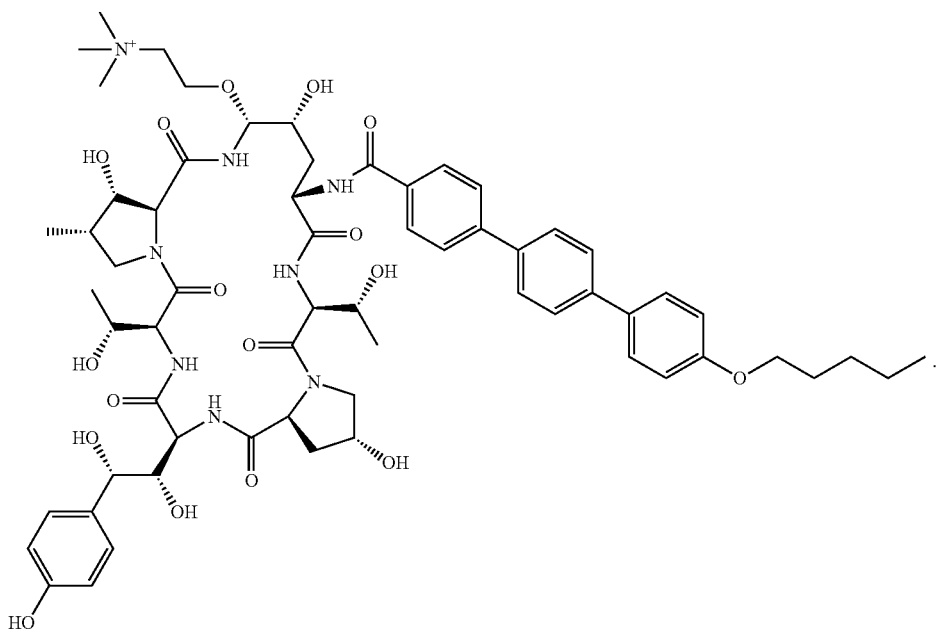

zole, bifonazole, butoconazole, clotrimazole, econazole, efinaconazole, fenticonazole, isavuconazole, isoconazole, itraconazole, ketoconazole, luliconazole, miconazole, omoconazole, oxiconazole, posaconazole, pramiconazole, ravuconazole, sertaconazole, sulconazole, terconazole, tioconazole, and voriconazole. As described herein, in some embodiments, a subject who has failed treatment with an azole therapy may be administered CD101 or a salt or neutral form thereof to treat the fungal infection. In some embodiments, a subject having a fungal infection may be administered CD101 or a salt or neutral form thereof if the fungal infection has failed treatment with an azole therapy.

As used herein, the term "1,3-β-D-glucan synthase enzyme complex" refers to the multi-subunit enzyme complex responsible for the synthesis of 1,3-β-D-glucan, which is an essential component in the fungal cell wall. A mutant 1,3-β-D-glucan synthase enzyme complex refers to a 1,3-β-D-glucan synthase enzyme complex having one or more mutations in one or more subunits of the enzyme complex. In some embodiments, the one or more mutations are in the FKS genes (FKS1, FKS2, FKS3), which encode the catalytic subunit of 1,3-β-D-glucan synthase enzyme complex.

By "effective" amount is meant the amount of drug required to treat or prevent an infection or a disease associated with an infection. The effective amount of drug used to practice the methods described herein for therapeutic or prophylactic treatment of conditions caused by or contributed to by a microbial infection varies depending upon the manner of administration, the age, body weight, and general health of the subject. Ultimately, the attending physician will decide the appropriate amount and dosage regimen. Such amount is referred to as an "effective" amount.

As used herein, the term "CD101 neutral form" includes the zwitterionic forms of CD101 in which the compound of Formula 1 has no net positive or negative charge. The zwitterion is present in a higher proportion in basic medium (e.g., pH 9) relative to CD101 or a salt of CD101. In some embodiments, the zwitterion may also be present in its salt form.

As used herein, the term "salt" refers to any pharmaceutically acceptable salt, such as a non-toxic acid addition salt, metal salt, or metal complex, commonly used in the pharmaceutical industry. Examples of acid addition salts include organic acids, such as acetic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxalo acetic, oxalosuccinic, propionic, pyruvic, ascorbic, succinic, benzoic, palmitic, suberic, salicylic, tartaric, methanesulfonic, toluenesulfonic, and trifluoroacetic acids, and inorganic acids, such as hydrochloric acid, hydrobromic acid, sulfuric acid, and phosphoric acid. Representative alkali or alkaline earth metal salts include sodium, lithium, potassium, calcium, and magnesium, among others.

As used herein, the amount in each dose refers to the amount of CD101 (Formula 1 shown above) that does not include the negative counterion (e.g., an acetate) if CD101 is in its salt form.

By "dose" is meant the amount of CD101 administered to the subject.

By "subject" or "patient" is meant a human.

By "clinical cure" is meant complete resolution of most or all of the clinical signs and symptoms of candidemia and/or invasive candidiasis which were present at baseline and no new signs/symptoms or complications attributable to candidemia and/or invasive candidiasis.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

As used herein, the term "mutant prevention concentration" or "MPC" refers to the concentration of a drug sufficient to suppress the development of all but very rare spontaneous mutants. The range of drug concentrations between the MIC and MPC represents a mutant selection window wherein de novo mutants are most likely to occur. Therapeutic regimens that maximize the duration of drug concentrations in excess of the MPC thereby minimize the potential for resistance development during the course of therapy.

Selection of resistance strains in vivo predominantly occurs over a range of drug concentrations falling between the MIC and MPC values. Dosing paradigms that result in plasma drug concentrations in excess of the MPC are therefore more desirable and effective in preventing the development of de novo mutants during the course of therapy (see, e.g., Drlica et al., *J. Antimicrob. Chemother.* 52:11-17, 2003). Currently approved treatment regimens for caspofungin, micafungin, and anidulafungin involve once-daily dosing at levels such that the Cmax is unlikely to be equivalent to or exceed the MPC at any point during treatment. The MPC determined for CD101 vs. *C. albicans* and *C. glabrata* was 16 µg/ml (see Example 2). Modeling of CD101 total plasma concentrations based on in vivo pharmacokinetic data allows us to calculate that an IV administration of C101≥50 mg would be sufficient to generate concentrations in excess of 16 µg/ml. For other strains and/or fungal species, the dosing regimen the produces a plasma mutant prevention concentration can be one in which the plasma concentration is in excess of 20 µg/ml, 24 µg/ml, 30 µg/ml, or 36 µg/ml CD101 or a salt or neutral form thereof has the potential to be dosed at levels exceeding the MPC, and thus have a stronger mutant prevention capacity than existing approved echinocandin treatment regimens.

Other than in the operating examples, or where otherwise indicated, all numbers expressing quantities of ingredients or reaction conditions used herein should be understood as modified in all instances by the term "about." As used herein, the term "about" indicates a deviation of ±5%.

Other features and advantages of the disclosure will be apparent from the following detailed description, the drawings, and the claims.

BRIEF DESCRIPTION OF THE DRAWINGS

FIG. 5 is a scatter-plot showing PK of CD101 over doses 1 mg/kg, 4 mg/kg, and 16 mg/kg.

FIG. 6 is a scatter-plot showing net change in fungal density ($\log_{10}$ CFU) versus different total doses of CD101 at different fractionation schedules.

FIG. 7 is a bar graph showing change in fungal density ($\log_{10}$ CFU) reduction from baseline caused by 2 mg/kg total dose of CD101 at different fractionation schedules.

FIG. 8 is a line graph showing simulated free-drug concentration time profiles relative to the MIC for the fractionated CD101 2 mg/kg regimen.

FIG. 10 is a table showing the activity of various antifungal agents against *Candida auris* clinical isolates.

DETAILED DESCRIPTION

Figure 1:
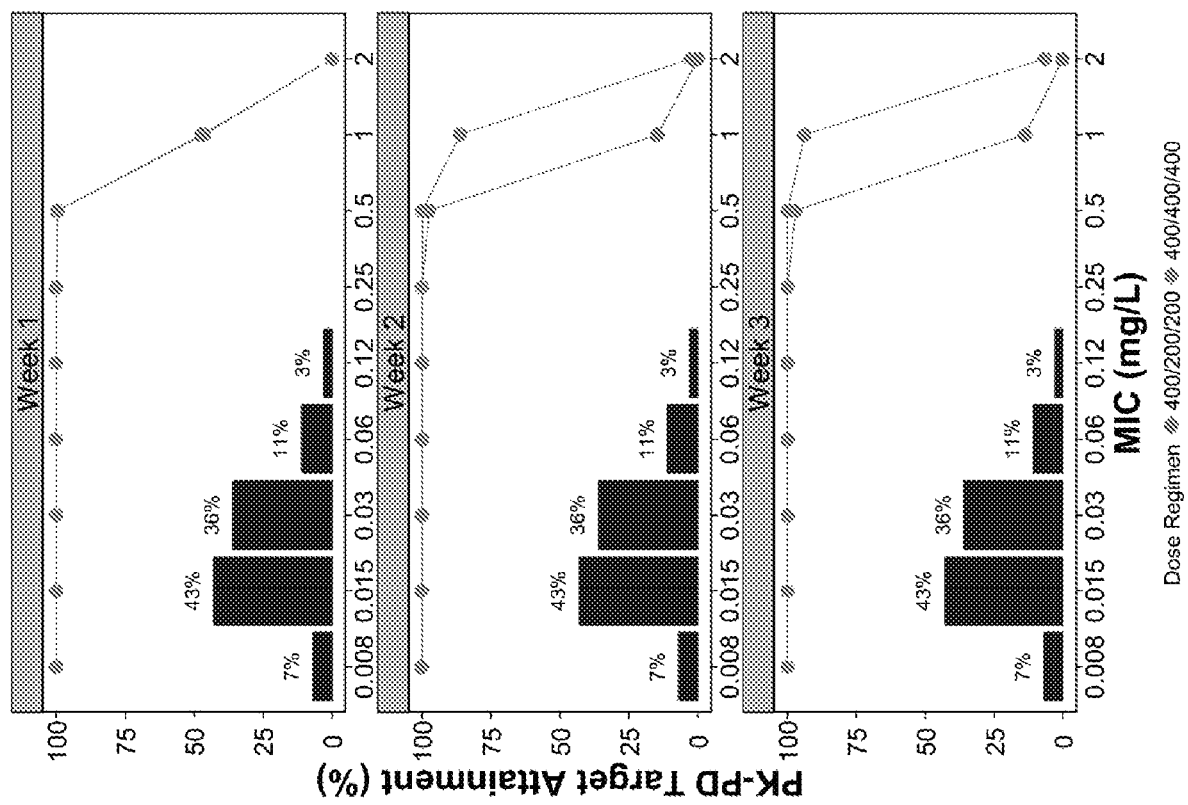
FIG. 1 are bar graphs showing the PK-PD target attainment for the two CD101 dosing regimens, stratified by week and Minimum Inhibitory Concentration (MIC).

Provided are methods of treating a fungal infection in a subject in need thereof by administering to the subject an intravenous infusion of CD101, in salt or neutral form, formulated as an aqueous composition.

CD101

CD101 is a semi-synthetic echinocandin that inhibits the synthesis of 1,3-β-D-glucan, an essential component of the fungal cell wall of yeast forms of *Candida* species and regions of active cell growth of *Aspergillus* hyphae. The synthesis of 1,3-β-D-glucan is dependent upon the activity of 1,3-β-D-glucan synthase, an enzyme complex in which the catalytic subunit is encoded by FKS1, FKS2, and FKS3 genes. Inhibition of this enzyme results in rapid, concentration-dependent, fungicidal activity for *Candida* spp. The structure of CD101 is depicted above.

Therapy

The treatment regimens and pharmaceutical compositions described herein can be used to treat or prevent fungal infections.

The fungal infection being treated can be an infection selected from tinea capitis, tinea corporis, tinea pedis, onychomycosis, perionychomycosis, pityriasis versicolor, oral thrush, vaginal candidiasis, respiratory tract candidiasis, biliary candidiasis, eosophageal candidiasis, urinary tract candidiasis, systemic candidiasis, mucocutaneous candidiasis, mucormycosis, paracoccidioidomycosis, North American blastomycosis, histoplasmosis, coccidioidomycosis, sporotrichosis, fungal sinusitis, or chronic sinusitis. For example, the infection being treated can be an infection by a *Candida* species (e.g., *C. albicans, C. glabrata, C. dubliniensis, C. krusei, C. parapsilosis, C. tropicalis, C. orthopsilosis, C. guilliermondii, C. rugosa, C. auris, C. lusitaniae*, or other *Candida* species).

In some embodiments, a fungal infection can be an antifungal drug-resistant fungal infection, which is a fungal infection that is refractory to treatment with an antifungal drug. In such infections, the fungus that causes the infection is resistant to treatment with one or more antifungal drugs (e.g., an antifungal drug-resistant strain of fungus (e.g., an antifungal drug-resistant strain of *Candida* spp.)). Antifungal drugs include, but are not limited to, azole compounds, echinocandins, polyene compounds, and flucytosine.

For example, an echinocandin-resistant fungal infection refers to a fungal infection that is refractory to treatment with an echinocandin. In such infections the fungus that causes the infection is resistant to treatment with one or more echinocandins. The one or more echinocandins are cyclic lipopeptides that inhibit the synthesis of glucan in the cell wall by inhibition of the 1,3-β-D-glucan synthase enzyme complex. The one or more echinocandins referred to in the term "echinocandin-resistant fungal infection" include micafungin, caspofungin, and anidulafungin, but does not include CD101, in salt or neutral form. Thus, using the methods of the disclosure, CD101, in salt or neutral form, can be used to treat micafungin-resistant, caspofungin-resistant, and/or anidulafungin-resistant fungal infections.

An antifungal drug-resistant fungal infection may also be an azole-resistant fungal infection, which refers to a fungal infection that is refractory to treatment with an azole compound. In such infections the fungus that causes the infection is resistant to treatment with one or more azole compounds. The azole compounds referred to in the term "azole-resistant fungal infection" are antifungal compounds that contain an azole group, which is a five-membered heterocyclic ring having at least one N and one or more heteroatoms selected from N, O, or S. Antifungal azole compounds function by binding to the enzyme 14α-demethylase and disrupt, inhibit, and/or prevent its natural function. The enzyme 14α-demethylase is a cytochrome P450 enzyme that catalyzes the removal of the C-14 α-methyl group from lanosterol before lanosterol is converted to ergosterol, an essential component in the fungal cell wall. Therefore, by inhibiting 14α-demethylase, the synthesis of ergosterol is inhibited. Examples of azole compounds include, but are not limited to, VT-1161, VT-1598, fluconazole, albaconazole, bifonazole, butoconazole, clotrimazole, econazole, efinaconazole, fenticonazole, isavuconazole, isoconazole, itraconazole, ketoconazole, luliconazole, miconazole, omoconazole, oxiconazole, posaconazole, pramiconazole, ravuconazole, sertaconazole, sulconazole, terconazole, tioconazole, and voriconazole.

An antifungal drug-resistant fungal infection may also be a polyene-resistant fungal infection, which refers to a fungal infection that is refractory to treatment with a polyene compound. In such infections, the fungus that causes the infection is resistant to treatment with one or more polyene compounds. Polyene compounds are compounds that insert into fungal membranes, bind to ergosterol and structurally related sterols in the fungal membrane, and disrupt membrane structure integrity, thus causing leakage of cellular components from a fungus that causes infection. Polyene compounds typically include large lactone rings with three to eight conjugated carbon-carbon double bonds and may also contain a sugar moiety and an aromatic moiety. Examples of polyene compounds include, but are not limited to, 67-121-A, 67-121-C, amphotericin B, arenomvcin B, aurenin, aureofungin A, aureotuscin, candidin, chinin, demethoxyrapamycin, dermostatin A, dermostatin B, DJ-400-$B_1$, DJ-400-$B_2$, elizabethin, eurocidin A, eurocidin B, filipin I, filipin II, filipin III, filipin IV, fungichromin, gannibamycin, hamycin, levorin $A_2$, lienomycin, lucensomycin, mycoheptin, mycoticin A, mycoticin B, natamycin, nystatin A, nystatin $A_3$, partricin A, partricin B, perimycin A, pimaricin, polifungin B, rapamycin, rectilavendomvcin, rimocidin, roflamycoin, tetramycin A, tetramycin B, tetrin A, and tetrin B.

An antifungal drug-resistant fungal infection may also be a flucytosine-resistant fungal infection, which refers to a fungal infection that is refractory to treatment with the synthetic antifungal drug flucytosine. A brand name for flucytosine is Ancobon®.

A *Candida* infection can be caused by an antifungal drug-resistant strain of fungus in the genus *Candida,* such as an antifungal drug-resistant strain of *C. albicans, C. parapsilosis, C. glabrata, C. guilliermondii, C. krusei, C. lusitaniae, C. auris, C. tropicalis,* or other *Candida* species. In some embodiments, a *Candida* infection can be caused by an azole-resistant strain of fungus in the genus *Candida,* such as an azole-resistant strain of *C. albicans, C. parapsilosis, C. glabrata, C. guilliermondii, C. krusei, C. lusitaniae, C. auris, C. tropicalis,* or other *Candida* species. In some embodiments, an azole-resistant strain of fungus is *Candida albicans,* e.g., *C. albicans* R357 strain. Azole-resistant *C. albicans* R357 strain contains mutations in the gene ERG11 (e.g., *C. albicans* ERG11 (CaERG11)). The CaERG11 gene encodes the enzyme 14α-demethylase, the target of azole antifungal compounds. Mutations in the CaERG11 gene that result in amino acid substitutions alter the abilities of the azole compounds to bind to and inhibit 14α-demethylase, thus resulting in resistance. In some embodiments, an azole-resistant *C. albicans* R357 strain have an increase in CaERG11 expression, e.g., 2-15 times (e.g., 3-15, 4-15, 5-15, 6-15, 7-15, 8-15, 9-15, 10-15, 11-15, 12-15, 13-15, or 14-15 times) more increased expression relative to a wild-type strain. In some embodiments, an azole-resistant *C. albicans* R357 strain have one or more mutations in the CaERG11 gene that lead to one or more amino acid substitutions, e.g., D116E, D153E, and/or E266D. In some embodiments, an azole-resistant *Candida albicans* R357 strain have no significant changes in CDR1 or MDR1 expression. Table 1 shows the percentage of inhibition and MIC values of three azole compounds, amphotericin B, caspofungin, and CD101 towards the azole-resistant *C. albicans* R357 strain and susceptibility status (S: susceptible; R: resistant) as classified by CLSI (Clinical and Laboratory Standards Institute) of the *C. albicans* R357 strain towards the listed compounds.

TABLE 1

| Antifungal agent | Endpoint (% inhibition) | MIC (µg/mL) | Susceptibility (CLSI) |
|---|---|---|---|
| Fluconazole | 50% | >64 | R |
| Voriconazole | 50% | >64 | R |
| Posaconazole | 50% | >64 | |
| Amphotericin B | 100% | 0.5 | S |
| Caspofungin | 50% | 0.25 | S |
| CD101 | 50% | 0.125 | |

Clinical isolates of *C. auris* that may be treated or prevented by the treatment regimens and pharmaceutical compositions described herein are described in the Examples section (e.g., Example 9) and also in Lee et al., *J Clin Microbiol.* 49:3139-42, 2011, Kathuria et al., *J Clin Microbiol.* 53:1823-30, 2015, and Vallabhaneni et al., *MMWR Morb Mortal Wkly Rep.* 65:1234-1237, 2016, each of which is incorporated by reference herein in its entirety. For example, FIG. 2 of Kathuria describes clinical isolates of *C. auris* which are shown in Table 2.

TABLE 2

| # | Clinical isolate |
|---|---|
| 1 | VPCI 717/P/14 |
| 2 | VPCI 462/P/14 |
| 3 | VPCI 1156/P/13 |
| 4 | VPCI 271/P/14 |
| 5 | VPCI 471/P/14 |

TABLE 2-continued

| # | Clinical isolate |
|---|---|
| 6 | VPCI 709/P/12 |
| 7 | VPCI 464/P/14 |
| 8 | VPCI 107/P/14 |
| 9 | VPCI 672/P/12 |
| 10 | VPCI 483/P/13 |
| 11 | VPCI 720/P/14 |
| 12 | VPCI 1132/P/13 |
| 13 | VPCI 512/P/14 |
| 14 | VPCI 249/P/14 |
| 15 | VPCI 553/P/14 |
| 16 | VPCI 1047/P/14 |
| 17 | VPCI 518/P/14 |
| 18 | VPCI 253/P/14 |
| 19 | VPCI 540/P/14 |
| 20 | VPCI 543/P/14 |
| 21 | VPCI 261/P/14 |
| 22 | VPCI 676/P/12 |
| 23 | VPCI 480/P/13 |
| 24 | VPCI 468/P/14 |
| 25 | VPCI 471/P/13 |
| 26 | VPCI 677/P/12 |
| 27 | VPCI 1131/P/13 |
| 28 | VPCI 708/P/12 |
| 29 | VPCI 669/P/12 |
| 30 | VPCI 670/P/12 |
| 31 | VPCI 475/P/13 |
| 32 | VPCI 478/P/13 |
| 33 | VPCI 514/P/14 |
| 34 | VPCI 476/P/13 |
| 35 | VPCI 507/P/14 |
| 36 | VPCI 1130/P/13 |
| 37 | VPCI 245/P/14 |
| 38 | VPCI 247/P/14 |
| 39 | VPCI 542/P/14 |
| 40 | VPCI 250/P/14 |
| 41 | VPCI 556/P/14 |
| 42 | VPCI 557/P/14 |
| 43 | VPCI 1048/P/14 |
| 44 | VPCI 260/P/14 |
| 45 | VPCI 550/P/14 |
| 46 | VPCI 509/P/14 |
| 47 | VPCI 513/P/14 |
| 48 | VPCI 478/P/14 |
| 49 | VPCI 671/P/12 |
| 50 | VPCI 673/P/12 |
| 51 | VPCI 463/P/14 |
| 52 | VPCI 266/P/14 |
| 53 | VPCI 711/P/12 |
| 54 | VPCI 264/P/14 |
| 55 | VPCI 265/P/14 |
| 56 | VPCI 472/P/13 |
| 57 | VPCI 106/P/14 |
| 58 | VPCI 263/P/14 |
| 59 | VPCI 712/P/12 |
| 60 | VPCI 477/P/13 |
| 61 | VPCI 479/P/13 |
| 62 | VPCI 548/P/14 |
| 63 | VPCI 508/P/14 |
| 64 | VPCI 481/P/13 |
| 65 | VPCI 484/P/13 |
| 66 | VPCI 718/P/14 |
| 67 | VPCI 714/P/14 |
| 68 | VPCI 248/P/14 |
| 69 | VPCI 536/P/14 |
| 70 | VPCI 528/P/14 |
| 71 | VPCI 511/P/14 |
| 72 | VPCI 510/P/14 |
| 73 | VPCI 554/P/14 |
| 74 | VPCI 546/P/14 |
| 75 | VPCI 1133/P/13 |
| 76 | VPCI 467/P/14 |
| 77 | VPCI 473/P/13 |
| 78 | VPCI 470/P/14 |
| 79 | VPCI 674/P/12 |
| 80 | VPCI 270/P/14 |
| 81 | VPCI 474/P/13 |
| 82 | VPCI 474/P/14 |
| 83 | VPCI 459/P/14 |
| 84 | VPCI 469/P/14 |
| 85 | VPCI 482/P/13 |
| 86 | VPCI 1059/P/14 |
| 87 | VPCI 473/P/14 |
| 88 | VPCI 692/P/12 |
| 89 | VPCI 683/P/12 |
| 90 | VPCI 105/P/14 |
| 91 | KCTC 17810 |
| 92 | JCM 15448 |
| 93 | KCTC 17809 |

The treatment regimens and pharmaceutical compositions described herein can be administered to prevent a fungal infection in a subject in need thereof. For example, subjects may receive prophylaxis treatment while being prepared for an invasive medical procedure (e.g., preparing for surgery, such as receiving a transplant, stem cell therapy, a graft, a prosthesis, receiving long-term or frequent intravenous catheterization, or receiving treatment in an intensive care unit), in immunocompromised subjects (e.g., subjects with cancer, with HIV/AIDS, or taking immunosuppressive agents), or in subjects undergoing long term antibiotic therapy. Alternatively, the treatment regimens and pharmaceutical compositions described herein can be administered to treat a blood stream infection or organ infection (e.g., lung, kidney, or liver infections) in a subject.

The following examples are put forth so as to provide those of ordinary skill in the art with a complete disclosure and description of how the methods and compounds claimed herein are performed, made, and evaluated, and are intended to be purely exemplary of the disclosure and are not intended to be limiting.

EXAMPLES

Example 1

Administration of CD101 to Healthy Adult Subjects

Clinical studies have shown that CD101 is safe and well tolerated as a single dose up to 400 mg and multiple doses up to 400 mg.

In a first study, CD101 was administered by IV injection to healthy adult subjects. In this study, subjects in 4 cohorts of 8 subjects (6 active, 2 placebo) each were randomized to receive single IV doses of CD101 or placebo (normal saline) infused over 60 (±5) minutes. Dose levels of CD101 assessed follow an ascending single-dose regimen (50, 100, 200, or 400 mg).

A total of 32 subjects were randomized, with 31 subjects completing all study assessments. One subject prematurely withdrew for personal reasons unrelated to safety or tolerability. Subjects were primarily White (97%), Hispanic (94%), and males and females were approximately equally represented (53% and 47%, respectively). There were no serious adverse events (SAEs), severe adverse events (AEs), or dose-response relationships for overall AEs. The majority of AEs were mild, and all AEs completely resolved by the end of the study. There were no drug-related AEs resulting from clinically significant hematology or clinical chemistry laboratory abnormalities at any dose. In addition, there were no safety issues related to electrocardiograms (ECGs), vital signs, or physical exam findings.

A second study of CD101 administered by IV injection to healthy adult subjects was also performed. In this study, subjects in 3 cohorts of 8 subjects (6 active, 2 placebo) each were randomized to receive multiple IV doses of CD101 or placebo (normal saline) infused over 60 (±5) minutes. Dose levels of CD101 assessed follow an ascending multiple-dose regimen (100 mg×2 doses, 200 mg×2 doses, or 400 mg×3 doses).

A total of 24 subjects were randomized and all subjects completed the study. Subjects were primarily White (88%), Hispanic or Latino (88%), and had a mean body mass index (BMI) of 27.208 kg/m$^2$ and a mean age of 42.8 years. Males and females were equally represented (50% each). There were no SAEs or severe AEs. The majority of AEs were mild, and all related AEs completely resolved by the end of the study. Four subjects in the CD101 group experienced mild, transient infusion reactions, characterized by flushing, sensation of warmth, nausea, and chest tightness. These infusion reactions were associated primarily with the 400 mg dose cohort and were most common with the third dose. These reactions occurred within minutes of infusion initiation and disappeared within minutes without interruption or discontinuation of the study drug infusion. There were no drug-related AEs resulting from clinically significant hematology or clinical chemistry laboratory abnormalities at any dose. In addition, there were no safety issues related to ECGs, vital signs, or physical exam findings.

Example 2

Clinical Pharmacology of CD101

As is described below, the pharmacokinetics of CD101 have been well-characterized in healthy subjects for doses up to 400 mg for 3 weeks.

Single Ascending Dose Pharmacokinetics

Pharmacokinetics were first determined by analyzing plasma and urine samples for concentration of CD101 obtained from subjects who received CD101 in each cohort at various time points after administration of the single dose of the study drug.

The plasma PK of CD101 was generally well-characterized following the 50, 100, 200, and 400 mg CD101 doses. Exposure to CD101 increased with increasing CD101 doses (Table 3). Time to reach $C_{max}$ (i.e., $T_{max}$) was observed at the end of infusion, as expected, at approximately 1 hour after the start of infusion for all doses. Elimination of CD101 appears multiphasic. AUC and $C_{max}$ increased in a dose proportional manner and total body clearance was similar throughout the dose levels with $t_{1/2}$ values of >80 hours through the first week of plasma collection (a longer terminal $t_{1/2}$ of 127-146 hours is calculated when incorporating data from later collection times). Total body clearance was approximately 4 mL/min across the CD101 doses, indicating linear kinetics for CD101 across the doses investigated. Volume of distribution ($V_z$ and $V_{ss}$) ranged from 33 to 48 L. The fraction of dose excreted in urine was <1% at all dose levels, indicating minor contribution of renal clearance in CD101 excretion.

TABLE 3

Summary of Plasma CD101 Exposures Following Administration of 50, 100, 200, and 400 mg 1-hour Intravenous Infusion of CD101

| Dose (mg) | $C_{max}$ (μg/mL) | $C_{144}$ (μg/mL) | $AUC_{0-168}$ (μg · h/mL) | $t_{1/2}$ (hours) |
|---|---|---|---|---|
| 50 | 2.76 | 0.481 | 145 | 86 |
| 100 | 4.84 | 0.854 | 254 | 92 |
| 200 | 10.9 | 2.01 | 592 | 91 |
| 400 | 22.7 | 3.83 | 1160 | 84 |

$AUC_{0-168}$ = area under the curve from time 0 to 168 hours;
$C_{144}$ = plasma concentration at 144 hours post start of infusion;
$C_{max}$ = maximum plasma concentration;
$t_{1/2}$ = half-life.

Multiple Ascending Dose Pharmacokinetics

Pharmacokinetics were determined by analyzing plasma and urine samples for concentration of CD101 obtained from subjects who received CD101 in each cohort at various time points after administration of CD101.

The plasma PK of CD101 was also well characterized following 2 or 3 weekly doses of CD101: 100 mg (Day 1/Day 8), 200 mg (Day 1/Day 8), and 400 mg (Day 1/Day 8/Day 15). Exposures following the first dose were very comparable to that observed in the SAD study, with AUC and $C_{max}$ generally increasing in a dose proportional manner (Table 4). Accumulation was minor, ranging from 14% to 34% (or 1.14 to 1.34) as measured by $C_{max}$ ratio of last/first dose and 30% to 55% (or 1.30 to 1.55), as measured by the $AUC_{0-168}$ ratio of last/first dose.

TABLE 4

Summary of Plasma CD101 Exposures Following Administration of 100 mg (Day 1/Day 8), 200 mg (Day 1/Day 8), and 400 mg (Day 1/Day 15) Weekly 1-hour Intravenous Infusion of CD101

| Dose (mg) | Day | $C_{max}$ (μg/mL) | $AUC_{0-168}$ (μg · h/mL) | Accumulation Ratio | |
|---|---|---|---|---|---|
| | | | | $C_{max}$ | $AUC_{0-168}$ |
| 100 | 1 | 5.67 | 299 | 1.14 | 1.30 |
| | 8 | 6.49 | 390 | | |
| 200 | 1 | 10.6 | 570 | 1.17 | 1.43 |
| | 8 | 12.4 | 813 | | |
| 400 | 1 | 22.7 | 1190 | 1.34 | 1.55 |
| | 15 | 30.5 | 1840 | | |

$AUC_{0-168}$ = area under the curve from time 0 to 168 hours;
$C_{max}$ = maximum plasma concentration.

Data from the above studies were used to develop a population PK model to describe the time course of CD101 concentrations after IV administration of single and multiple, once-weekly doses. In brief, the data were best described using a 4-compartment model with 0-order drug input via the IV infusion and first-order, linear elimination. In order to account for the relationships between the structural PK parameters and subject body weight, all parameters in the model were scaled to subject body weight using standard allometric coefficients (a power of 0.75 for the clearance terms and 1.0 for the volume terms). This model fit the observed data with very little bias and excellent precision.

Monte Carlo simulations were conducted to assess the probability of PK-pharmacodynamic (PD) target attainment using a variety of exploratory dosing regimens. Two dosing regimens were selected for further investigation (Table 5). The weekly free-drug area under the CD101 concentration-time curve from time 0 to 168 hours ($fAUC_{0-168}$) after each dose was simulated for 2000 hypothetical patients; patient body weight was simulated using a database of patient demographic characteristics and plasma protein binding was assumed to be 99.1%. Nonclinical studies of *Candida albicans* infections in mice have shown that a CD101 $fAUC_{0-168}$:MIC ratio of 10 has been associated with a 2-log reduction in fungal burden in infected kidneys. This value of 10 was therefore chosen as the PK-PD target of interest for the Monte Carlo simulations.

Two regimens (400 mg/400 mg/400 mg and 400 mg/200 mg/200 mg) are predicted to provide adequate PK-PD target attainment up to a MIC of 0.5 mg/L (3 dilution steps higher than the $MIC_{90}$ of 0.06 for *C. albicans* and *glabrata* based upon surveillance data from Sentry 2014). Additionally, due to the accumulation with repeated doses, the 400 mg IV once weekly regimen would be expected to achieve higher PK-PD target attainment at an MIC of 1 mg/L in Weeks 2 and 3 of therapy, and thus is expected to provide additional benefit beyond the first week of therapy against pathogens with an MIC ≥1 mg/mL. The PK-PD target attainment for the 2 chosen regimens are shown in Table 5 and FIG. 1.

TABLE 5

Predicted Pharmacokinetic-Pharmacodynamic Target Attainment for CD101 Regimens, Stratified by Week and Minimum Inhibitory Concentration

| Regimen[a] | Week | MIC (mg/L)[b] | | | | | |
|---|---|---|---|---|---|---|---|
| | | 0.06 | 0.12 | 0.25 | 0.5 | 1 | 2 |
| 400/400/400 | 1 | *100* | *100* | *100* | 99.4 | 46.6 | 0.10 |
| | 2 | *100* | *100* | *100* | *100* | 86.3 | 2.60 |
| | 3 | *100* | *100* | *100* | *100* | 93.8 | 6.85 |
| 400/200/200 | 1 | *100* | *100* | *100* | *100* | 47.3 | 0.05 |
| | 2 | *100* | *100* | *100* | *97.4* | 14.7 | 0 |
| | 3 | *100* | *100* | *100* | *97.2* | 14.0 | 0 |

MIC = minimum inhibitory concentration.
[a]Regimens defined by the weekly dose (e.g., 400/200/200 represents 400 mg for the first dose followed by 200 mg IV once weekly for two doses).
[b]Italicized text indicates PK-PD target attainment above 90%.

Example 3

Treatment of Subjects With Candidemia and/or Invasive Candidiasis

Subjects with candidemia and/or invasive candidiasis receive CD101 Injection (400 mg on each of Day 1 and Day 8, with an optional dose of 400 mg on Day 15; or 400 mg on each of Day 1, Day 8, and Day 15, with an optional dose of 400 mg on Day 22; or 400 mg on each of Day 1, Day 8, Day 15, and Day 22, with an optional dose of 400 mg on Day 29; or 400 mg on each of Day 1, Day 8, Day 15, Day 22, and Day 29, with an optional dose of 400 mg on Day 36; or 400 mg on Day 1 and 200 mg on Day 8, with an optional dose of 200 mg on Day 15; 400 mg on Day 1 and 200 mg on each of Day 8 and Day 15, with an optional dose of 200 mg on Day 22; 400 mg on Day 1 and 200 mg on each of Day 8, Day 15, and Day 22, with an optional dose of 200 mg on Day 29; 400 mg on Day 1 and 200 mg on each of Day 8, Day 15, Day 22, and Day 29, with an optional dose of 200 mg on Day 36). Mycological diagnosis of candidemia and/or invasive candidiasis is established by ≥1 blood culture positive for *Candida* spp. within 96 hours from time of collection before administration of the first dose.

CD101 is supplied as a sterile solution or as a lyophilized formulation. Vials of CD101 Injection are diluted with normal saline in an infusion bag. CD101 is administered by IV infusion over 60 (±5) minutes on day 1, day 8, and optionally, day 15.

In some embodiments, CD101 Injection is provided as a sterile aqueous or lyophilized product for dilution (e.g., in sodium chloride 0.9%) prior to infusion. In some embodiments, one or more vials of aqueous CD101 are diluted in infusion bags.

CD101 is administered over a time period of 30 to 180 minutes (e.g., over 30±5 minutes, 60±5 minutes, 90±5 minutes, 120±5 minutes, 150±5 minutes, 180±5 minutes, 30±10 minutes, 60±10 minutes, 90±10 minutes, 120±10 minutes, 150±10 minutes, or 180±10 minutes).

Example 4

Assessment of Infection Following Azole-Resistant *Candida albicans* R357 Infection The azole-resistant *C. albicans* R357 was obtained from a frozen working stock and thawed at room temperature. A 0.1 mL aliquot of the stock was transferred to a sabouraud agar (SA) plate and incubated at 35-37° C. overnight. The culture was re-suspended in 1 mL cold PBS (>2.0×10$^9$ CFU/mL, $OD_{620}$ 3.0-3.2) and diluted with PBS to target inoculum sizes of 5×10$^6$, 5×10$^5$, 5×10$^4$, and 5×10$^3$ CFU/mL. The actual colony counts were determined by plating dilutions to SA plates followed by 20-24 hr incubation.

Groups of male ICR (Institute of Cancer Research) mice (n=3 per group) weighing 22±2 g were used. Immune suppression was induced by two intraperitoneal injections of cyclophosphamide at 150 mg/kg 4 days (Day—4) and at 100 mg/kg 1 day (Day—1) before *C. albicans* infection. On Day 0, animals were intravenously inoculated (0.2 mL/mouse) with the R357 suspension. The animals were euthanized by $CO_2$ asphyxiation at 2 and 72 hr post-inoculation. A summary of the experimental design is shown in Table 6.

TABLE 6

| Experimental Design | | | |
|---|---|---|---|
| Group | Inoculum size (CFU/animal) | Time at sacrifice Post-infection | ICR Mice (male) |
| 1a | 1E6 | 2 hr | 3 |
| 1b | 1E6 | 72 hr | 3 |
| 2a | 1E5 | 2 hr | 3 |
| 2b | 1E5 | 72 hr | 3 |
| 3a | 1E4 | 2 hr | 3 |
| 3b | 1E4 | 72 hr | 3 |
| 4a | 1E3 | 2 hr | 3 |
| 4b | 1E3 | 72 hr | 3 |

Figure 2:
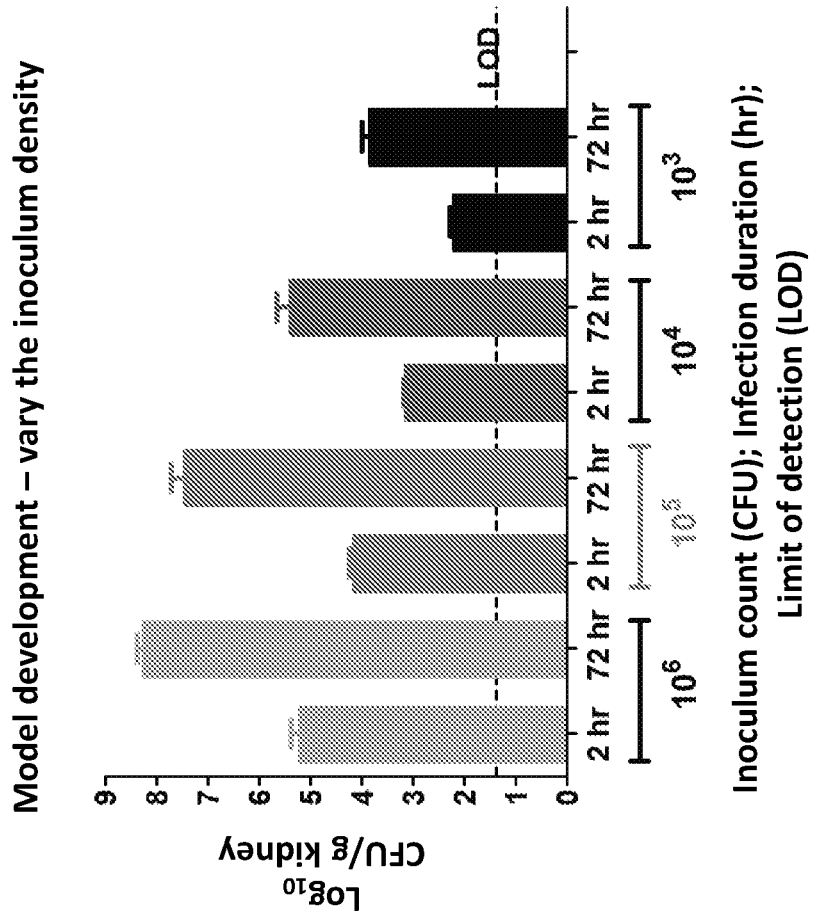
FIG. 2 is a bar graph showing kidney burdens in mice infected with different inoculum densities of azole-resistant *C. albicans* strain R357.

Paired kidneys were harvested and weighed. The harvested kidneys were homogenized in 1 mL sterile PBS (pH 7.4) and 10-fold dilutions were prepared and separately plated onto SA plates for further 20-24 hr incubation and then the fungal counts (CFU/g) in kidneys were calculated. Kidney fungal burdens from different inoculum densities of azole-resistant *C. albicans* strain R357 are shown in FIG. 2.

Example 5

Efficacy of Amphotericin B, Fluconazole, and CD101 in the Disseminated Infection Model with *C. albicans* R357

Materials

Test Articles. CD101 was dissolved in the vehicle containing 10% DMSO and 1% Tween 20 in 0.9% NaCl (see formulation table below). Amphotericin B and fluconazole were in powder form. Amphotericin B was dissolved in 0.9% NaCl. Fluconazole was dissolved in water (WFI: water for injection). A summary of the test articles is shown in Table 7.

Centrifuge (Model 5922, Kubota, Japan), Individually Ventilated Cages (IVC, 36 Mini Isolator systems) (Tecniplast, Italy), Laminar flow (Tsao-Hsin, Taiwan), Orbital shaking incubator (Firstek Scientific, Taiwan), Pipetman (Rainin,

TABLE 7

Test Articles

| Test Article | Vehicle | Solubility[a] | Color | Light Protection[b] | Temp. | Formulation mg/mL |
|---|---|---|---|---|---|---|
| CD101 | 10% DMSO/1% Tween 20 in 0.9% NaCl | S | colorless- | Yes | 4° C. | 0.3, 1 and 3 |
| Amphotericin B | 0.9% NaCl | S | light yellow | Yes | 4° C. | 0.1 and 0.3 |
| Fluconazole | WFI | S | colorless | Yes | RT | 2 |

[a]This is based on visual observation (S: soluble; SS: slightly soluble; I: insoluble (suspension or precipitation)).
[b]Test article is kept in tube or vial with brown color, or covered with aluminum foil.
c: 4° C.: prepared fresh and stored in the refrigerator or kept on ice; ET: prepared fresh and stored between 20-25° C.

Organism. The *C. albicans* strains R357 was cryopreserved as single-use frozen working stock cultures stored at −70° C.

Animals. Male ICR mice weighing 22±2 g were acclimated for 3 days prior to use and were confirmed to be in good health. Space allocation for 3 or 5 animals was 27×20×14 cm. All animals were maintained in a hygienic environment with controlled temperature (20-24° C.), humidity (30%-70%) and 12 hours light/dark cycles. Free access to sterilized standard lab diet and autoclaved tap water were granted. All aspects of this work including housing, experimentation, and animal disposal were performed in general accordance with the "Guide for the Care and Use of Laboratory Animals: Eighth Edition" (National Academies Press, Washington, D.C., 2011).

Chemicals. Amphotericin B powder (Cat #A-9528, Sigma, USA), Bacto agar (Cat #214040, BD DIFCO, USA), cyclophosphamide (Cat #C-0768, Sigma, USA), dimethyl sulfoxide (Cat #1.02931.1000, Merck, Germany), fluconazole powder (Cat #F8929, SIGMA-Aldrich, USA), Fluid Sabouraud medium (Cat #264210, BD DIFCO, USA), Phosphate buffer saline (PBS) (Cat #P4417, Sigma, USA), Sodium chloride (Cat #S7653, SIGMA-Aldrich, USA), Tween 20 (Cat #P-7949, Sigma, USA) and Water for injection (WFI) (Tai-Yu, Taiwan).

Equipment. Biological safety cabinet (NuAire, USA), Absorbance microplate readers (Tecan, Infinite F50, USA), USA), Polytron homogenizer (Kinematica, Switzerland) and Ultra-Low temperature freezer (NuAire, USA).

Methods

The azole-resistant *C. albicans* (R357) strain was obtained from a frozen working stock and thawed at room temperature. A 0.1 mL aliquot stock was transferred to a sabouraud agar (SA) plate and incubated at 35-37° C. overnight. The culture was re-suspended in 1 mL cold PBS (>2.0×10$^9$ CFU/mL, $OD_{620}$ 3.0-3.2) and diluted with PBS to 5×10$^5$ CFU/mL. The actual colony counts were determined by plating dilutions to SA plates followed by 20-24 hr incubation. The actual inoculum count was 7.05×10$^5$ CFU/mL.

Groups of male ICR mice (n=5 per group) weighing 22±2 g were used. Immune suppression was induced by two intraperitoneal injections of cyclophosphamide at 150 mg/kg 4 days (Day—4) and at 100 mg/kg 1 day (Day—1) before *C. albicans* infection. On Day 0, animals were intravenously inoculated (0.2 mL/mouse) with 5 inoculum sizes at 1.41×10$^5$ CFU/0.2 mL/mouse of *C. albicans* (R357). CD101 was administered by intraperitoneal (IP) injection at 3, 10 and 30 mg/kg. Amphotericin B (AM-B) was administered by intravenous (IV) injection at 1 and 3 mg/kg. Fluconazole (FLU) was administered by oral gavage (PO) at 20 mg/kg. All test articles were administered once 2 hours after inoculation. The dosing volume was 10 mL/kg for all groups. A summary of the experimental design is shown in Table 8.

TABLE 8

Experimental Design

| Group | Test Article | Animal Sacrifice | Dose Route | Conc. mg/mL | Dosage mL/kg | Dosage mg/kg | ICR Mice (male) |
|---|---|---|---|---|---|---|---|
| 1 | N/A | 2 hr | — | — | — | — | 5 |
| 2 | Vehicle | 72 hr | IP | — | 10 | — | 5 |
| 3 | Vehicle | 48 hr | IP | — | 10 | — | 5 |
| 4 | Amphotericin B | 72 hr | IV | 0.1 | 10 | 1 | 5 |
| 5 | Amphotericin B | 48 hr | IV | 0.1 | 10 | 1 | 5 |
| 6 | Amphotericin B | 72 hr | IV | 0.3 | 10 | 3 | 5 |
| 7 | Amphotericin B | 48 hr | IV | 0.3 | 10 | 3 | 5 |
| 8 | Fluconazole | 72 hr | PO | 2 | 10 | 20 | 5 |
| 9 | Fluconazole | 48 hr | PO | 2 | 10 | 20 | 5 |
| 10 | CD101 | 72 hr | IP | 0.3 | 10 | 3 | 5 |
| 11 | CD101 | 48 hr | IP | 0.3 | 10 | 3 | 5 |
| 12 | CD101 | 72 hr | IP | 1 | 10 | 10 | 5 |

TABLE 8-continued

Experimental Design

| Group | Test Article | Animal Sacrifice | Dose Route | Conc. mg/mL | Dosage mL/kg | Dosage mg/kg | ICR Mice (male) |
|---|---|---|---|---|---|---|---|
| 13 | CD101 | 48 hr | IP | 1 | 10 | 10 | 5 |
| 14 | CD101 | 72 hr | IP | 3 | 10 | 30 | 5 |
| 15 | CD101 | 48 hr | IP | 3 | 10 | 30 | 5 |

Target inoculum size 1E05 CFU/mouse (the actual inoculum size was 1.41E05 CFU/mouse).
Vehicle: 10% DMSO/1% Tween 20 in 0.9% NaCl
Test articles were dosed once 2 hrs after infection. Animals were sacrificed at assigned time points after infection.

The animals were euthanized by $CO_2$ asphyxiation 48 and 72 hr post-inoculation. Paired kidneys were harvested and weighed. The harvested kidneys were homogenized in 1 mL sterile PBS (pH 7.4) and 10-fold dilutions were prepared and separately plated onto SA plates. The fungal counts (CFU/g) in kidneys were calculated and the decrease percentage was calculated by the following formula:

Decrease (%)=[(CFU/g of vehicle−CFU/g of treatment)/(CFU/g of vehicle)]×100%

Figure 3:
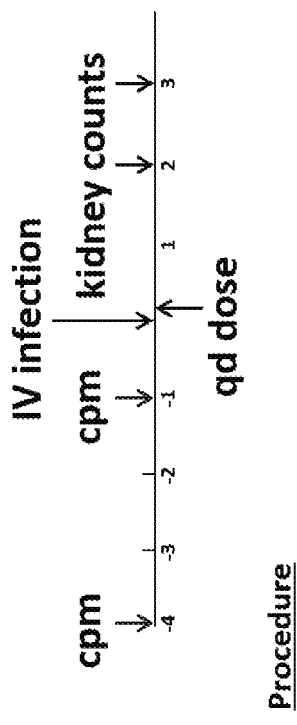
FIG. 3 shows an outline of the experimental protocol used to evaluate the efficacy of CD101, amphotericin B, and fluconazole in a *C. albicans* R357 infection model.
Figure 4A:
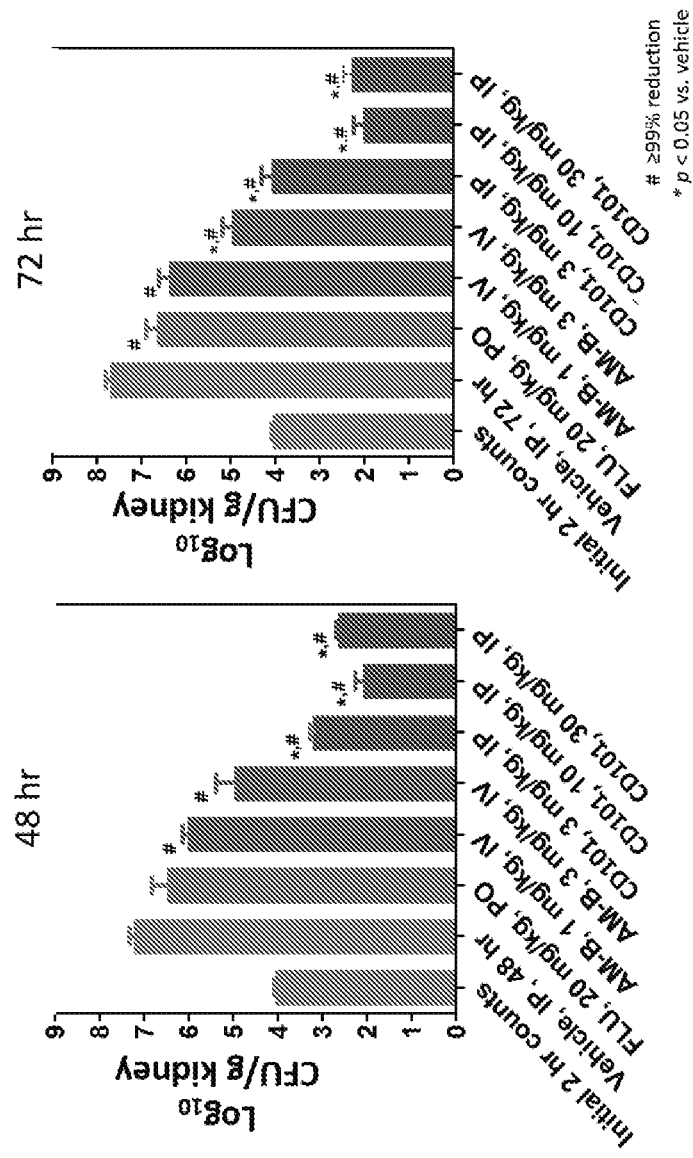
FIGS. 4A and 4B are bar graphs showing effects of CD101, amphotericin B (AM-B), and fluconazole (FLU) on kidney burdens in mice infected with azole-resistant *C. albicans* strain R357.
Figure 4B:
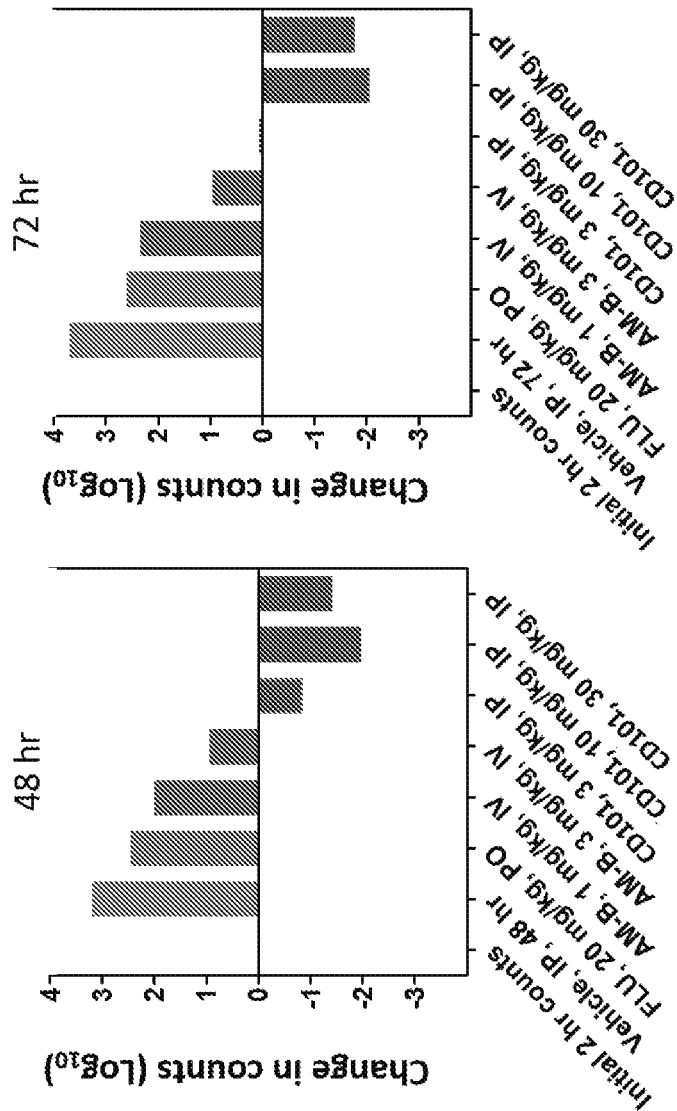

An outline of the experimental protocol is shown in FIG. 3. FIGS. 4A and 4B show the absolute fungal counts and the difference in fungal counts, respectively, of the test article treatment groups measured 48 or 74 hr after infection. A decrease of 99% or more (≥99%, 2-log) in the fungal counts of treated animals compared to those in the vehicle group measured 48 or 72 hr after infection indicated significant antimicrobial activity. One-way ANOVA followed by Dunnett's test was also applied to assess statistical significance.

Significant antimicrobial effects (P<0.05) were observed with CD101 treatment groups at 3, 10, and 30 mg/kg IP at 48 and 72 hr after infection. A two log reduction in fungal counts was observed with all CD101 treatment groups at the 48 and 72 hr time points. Significant effects were observed following amphotericin B treatment at 1 and 3 mg/kg IV at 48 and 72 hr after infection. Amphotericin B treatment at 3 mg/kg IV resulted in a two log reduction in counts at 72 hr time point. Administration of fluconazole at 20 mg/kg PO elicited a moderate reduction (51% and 84%) in colony counts 48 and 72 hr after infection compared to the vehicle control group that was not significant with one-way ANOVA followed by Dunnett's test analysis (P>0.05).

Example 6

Pharmacological Basis of CD101 Efficacy

Methods

Pharmacokinetic Study. Healthy female ICR mice were given a single dose of CD101 via intraperitoneal (IP) injection. The following doses, at three mice per dose, were studied: 1, 4, and 16 mg/kg. CD101 plasma concentrations were determined at 0, 1, 3, 6, 12, 24, 48, 72, 96 hours post-dose using a validated LC/MS assay with a lower limit of quantification of 0.02 μg/mL.

Dose-Fractionation Study. Male or female ICR mice (5 per regimen and observation time) weighing 22±2 g were rendered neutropenic for the study by injecting the mice with cyclophosphamide treatment four days (—Day 4) (150 mg/kg IP) and one day (—Day 1) prior to infection at 100 mg/kg IP. Neutropenia was sustained for the duration of the study with cyclophosphamide doses (100 mg/kg IP) every 48 hours on days +1, +3, +5 and +7 after infection. Each animal was inoculated intravenously with $1\times10^3$ CFU of C. albicans (Strain R303, MIC=0.125 mg/L). CD101 (or vehicle) was administered 24 hours post-infection via IP injection. The doses studied are shown in Table 9.

TABLE 9

Summary of CD101 dosing regimens evaluated

| Total Dose | Dosing Interval | Fractionated Doses |
|---|---|---|
| 0.7 mg/kg | Single Dose | 0.7 mg/kg × 1 |
|  | Twice Weekly | 0.35 mg/kg × 2 |
|  | Daily | 0.1 mg/kg × 7 |
| 2 mg/kg | Single Dose | 2 mg/kg × 1 |
|  | Twice Weekly | 1 mg/kg × 2 |
|  | Daily | 0.29 mg/kg × 7 |
| 7 mg/kg | Single Dose | 7 mg/kg × 1 |
|  | Twice Weekly | 3.5 mg/kg × 2 |
|  | Daily | 1 mg/kg × 7 |

Mice were sacrificed 168 hours (7 days) following the start of treatment. Control arm mice were sacrificed 0, 24, and 48 hours post administration of vehicle. Paired kidneys are aseptically harvested, homogenized, and plated for colony counts to determine the fungal burden (CFU/g).

Pharmacokinetic-Pharmacodynamic Analyses. Using the data collected from the PK study, a PK model was developed in S-ADAPT. Using the developed PK model, concentration-time profiles and $AUC_{0-168h}$ values were computed for each dosing regimen administered in the dose-fractionation study. Free-drug plasma concentrations were generated using a murine protein binding value of 99.1%. Relationships between the change in $\log_{10}$ CFU from start of therapy and $AUC_{0-168h}$ were explored.

Results

CD101 exhibited linear PK over the dose ranged studied (1 to 16 mg/kg IP). A 4-compartment model best described the PK data. Model fits are displayed in FIG. 5.

The results of the dose-fractionation study are displayed in FIG. 6, which shows that fungi grew well in the no-treatment control group. The magnitude of net change in fungal density ($\log_{10}$ CFU) was similar regardless of fractionation schedule within the CD101 0.7 and 7 mg/kg dosing groups. However, results within the CD101 2 mg/kg group varied by the fractionation schedule.

The change in $\log_{10}$ CFU reduction from baseline at 168 hours by fractionation schedule for the CD101 2 mg/kg group is displayed in FIG. 7. When a total dose of 2 mg/kg was delivered daily (0.29 mg/kg/day), the magnitude of net change in fungal density ($\log_{10}$ CFU) was similar to the no-treatment control group. However, when 2 mg/kg is delivered as a single dose, there was a greater than 2-$\log_{10}$ CFU reduction from baseline at 168 hours. The 2 mg/kg×1 and 0.29 mg/kg daily×7 regimens had similar cumulative CD101 exposures at 168 hours, as displayed in FIG. 6. Despite having similar exposures, which influences efficacy, these regimens showed very different effects.

Free-drug plasma concentration-time profiles of the three fractionated CD101 2 mg/kg dosing regimens are displayed in FIG. 8. All three regimens display very different exposure profiles. In particular, the single dose regimen results in larger CD101 exposures early in therapy. Free-drug plasma $AUC_{0-24}$ is 0.0654, 0.0303, and 0.00948 mg·h/L following administration of CD101 2 mg/kg as a single dose, twice weekly, and daily regimen, respectively. Further, administration of a single dose results in free-drug plasma concentrations which remain above those for the twice weekly and daily regimens for 84 and 48 hours, respectively.

Three CD101 regimens with similar total exposures, yet very different exposure shapes, display considerably different efficacy. This suggests that the shape of the CD101 AUC is a determinant of efficacy, with front loaded regimens demonstrating greater efficacy. The magnitude of the net change in fungal burden was similar regardless of fractionation schedule within the CD101 0.7 and 7 mg/kg dosing groups, but differed within the 2 mg/kg group. A 2 mg/kg dose was considerably more effective when given once per week compared to the same dose divided into twice-weekly or daily regimens.

Example 7

Efficacy of CD101 in Mouse Models of Aspergillosis and Azole-Resistant Disseminated Candidiasis Methods The in vivo efficacy of CD101 was evaluated using neutropenic mouse models of azole-resistant candidiasis and aspergillosis. An azole-resistant strain of *C. albicans* (R357; resistant to fluconazole [Flu], voriconazole, and posaconazole but susceptible to amphotericin B [AmB] and echinocandins) isolated from human blood was used for the mouse candidiasis model. A test strain of *Aspergillus fumigatus* (ATCC 13073) was used for the mouse aspergillosis model. Mice were rendered neutropenic by cyclophosphamide and then infected by injections of *C. albicans* ($10^5$ CFU/mouse) or *A. fumigatus* ($10^4$ CFU/mouse) into the tail vein. Test articles were administered starting 2 hours after infection. In the mouse candidiasis model, groups of 5 mice each received one dose of AmB (3 mg/kg IV), Flu (20 mg/kg orally), or CD101 (3, 10 or 30 mg/kg by intraperitoneal administration [IP]). After 72 hours post-infection, mice were euthanized and *C. albicans* counts in kidney tissue (CFU/g) were measured. In the mouse aspergillosis model, groups of 10 mice each received one dose of AmB (2 mg/kg IP) or CD101 (2 mg/kg IV and IP). Survival was monitored daily for 10 days. Differences between vehicle and test article groups were assessed for significance by one-way ANOVA followed by Dunnett's test and Fisher's Exact test in the candidiasis and aspergillosis models, respectively.

Results

Figure 9:
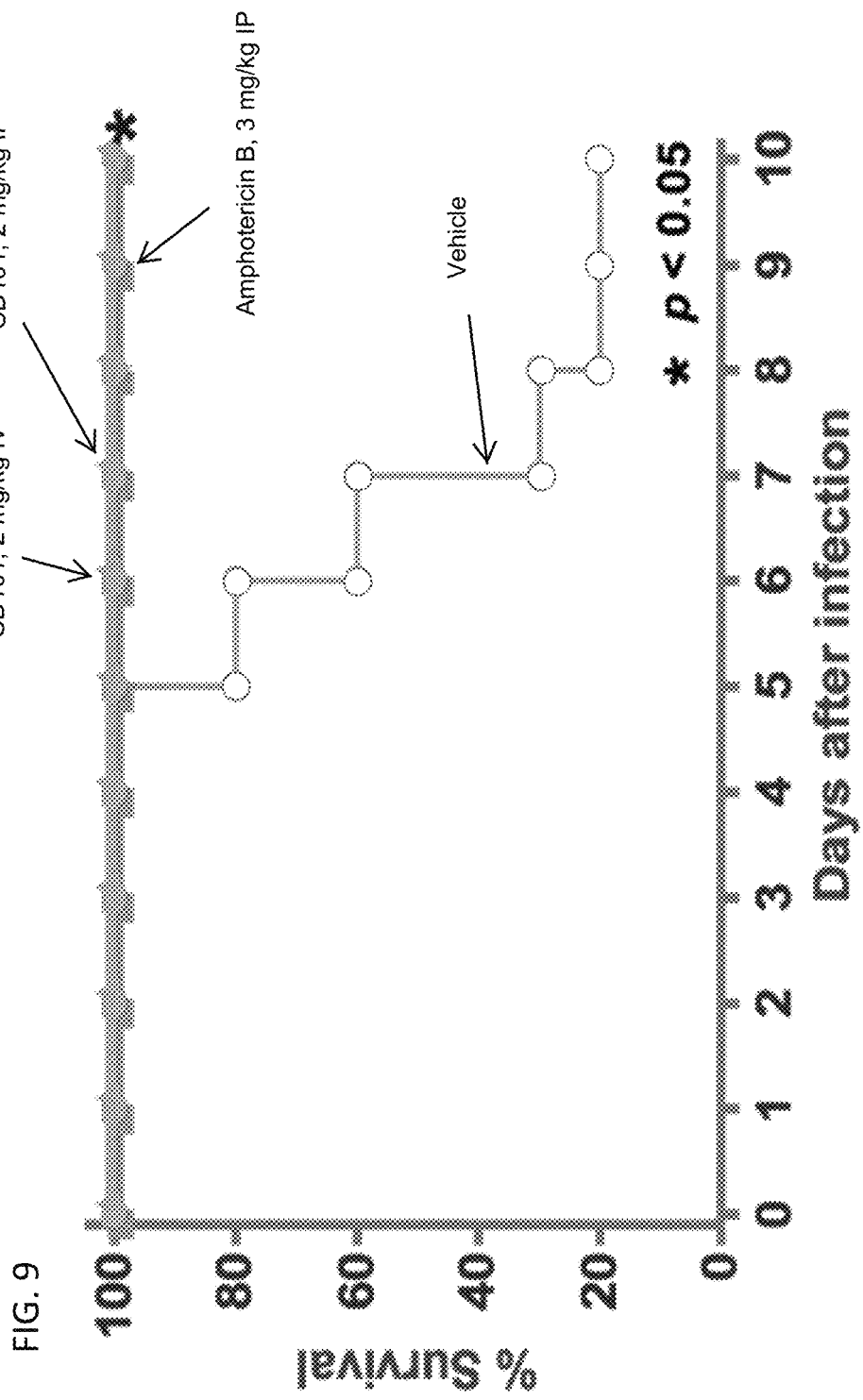
FIG. 9 is a graph showing percent survival over time in mice infected with *Aspergillus fumigatus* and treated with 2 mg/kg CD101 (IV or IP).

One dose of CD101 3 mg/kg produced a >99.9% (or >3-log; P<0.001) reduction in *C. albicans* CFU compared with vehicle through at least 72 hours post-dose following a single IP dose. AmB showed similar, albeit less robust, efficacy (>99% or >2-log reduction in CFU; P<0.05), whereas fluconazole was less efficacious (83.9% or <2-log reduction in CFU). In the aspergillosis model, CD101 administered 2 mg/kg IV or IP showed similar efficacy to that of AmB 2 mg/kg IP, both with significantly longer survival than vehicle (P<0.05; FIG. 9).

Conclusions

A single dose of CD101 3 mg/kg produced significant reduction in *C. albicans* burden compared with vehicle (P<0.001) in the neutropenic mouse model of azole-resistant candidiasis, demonstrating efficacy comparable, if not better, to that of AmB at the same dose. One dose of CD101 also demonstrated efficacy in the mouse model of aspergillosis. These data support the continued development of CD101 for treatment of serious infections caused by *Candida,* including azole-resistant strains, and *Aspergillus* spp.

Example 8

Efficacy of CD101 Against *Candida auris* Clinical Isolates

Materials and Methods

Organisms and Antifungal Agents

*C. auris* clinical isolates obtained from Japan, South Korea, India and the Center for Medical Mycology (n=14) were evaluated. The following *Candida* QC strains approved for yeast and moulds by the Clinical and Laboratory Standards Institute (CLSI, Document M38-A2) were used: *C. parapsilosis* ATCC 22019, *C. krusei* ATCC 6258. Test compounds were prepared fresh prior to use in MIC assays and included: CD101, 5-flucytosine (5FC), amphotericin B (AMB), anidulafungin (ANID), caspofungin (CAS), fluconazole (FLU), itraconazole (ITRA), micafungin (MICA), posaconazole (POSA) and voriconazole (VORI).

Minimum Inhibitory Concentration (MIC) Assays

Broth microdilution MIC assays performed according to CLSI M38-A2 methodology were used to evaluate the susceptibility of the fungal strains to the selected antifungals. Briefly, *C. auris* strains were plated on Sabouraud Dextrose Agar (SDA) and incubated at 37° C. for 2 days. *C. auris* cells were then harvested by centrifugation and normal saline (0.85% NaCl) washes. MIC assay inoculums were prepared using a hemocytometer. MIC assays were read after 24 and/or 48 hours incubation at 50 and/or 100% inhibition (FIG. 10). To check the inoculum count, ten-fold dilutions of *C. auris* working conidial suspension were plated onto SDA media. Inoculum plates were incubated at 37° C. for 2 days prior to determining colony count.

Example 9

Efficacy CD101, Caspofungin (CAS), Micafungin (MICA), and Fluconazole (FLU) Against *Candida auris* Clinical Isolates and FKS1 HS1 Sequence Analysis This study was to determine in vitro susceptibility of clinical *C. auris* isolates to CD101, caspofungin (CAS), micafungin (MICA), and fluconazole (FLU), and to analyze the sequence of hot spot 1 (HS1) within FKS1.

Materials and Methods

*Candida auris* isolates. Thirty-eight *C. auris* strains, obtained from VP Chest Institute, University of Delhi (Delhi, India) were used in the study (Table 10). Strains were grown on yeast extract peptone dextrose (YPD) agar plates prior to testing.

TABLE 10

| Strain # | C. auris strain # (India) |
|---|---|
| 1 | VPCI 669/P/12 |
| 2 | VCPI 671/P/12 |
| 3 | VCPI 674/P/12 |
| 4 | VCPI 683/P/12 |
| 5 | VCPI 692/P/12 |
| 6 | VCPI 712/P/12 |
| 7 | VCPI 471/P/13 |
| 8 | VCPI 475/P/13 |
| 9 | VCPI 478/P/13 |
| 10 | VCPI 479/P/13 |
| 11 | VCPI 480/P/13 |
| 12 | VCPI 482/P/13 |
| 13 | VCPI 483/P/13 |
| 14 | VCPI 1130/P/13 |
| 15 | VCPI 1132/P/13 |
| 16 | VCPI 1133/P/13 |
| 17 | VCPI 105/P/14 |
| 18 | VCPI 107/P/14 |
| 19 | VCPI 510/P/14 |
| 20 | VCPI 511/P/14 |
| 21 | VCPI 512/P/14 |
| 22 | VCPI 513/P/14 |
| 23 | VCPI 514/P/14 |
| 24 | VCPI 250/P/14 |
| 25 | VCPI 265/P/14 |
| 26 | VCPI 266/P/14 |
| 27 | VCPI 462/P/14 |
| 28 | VCPI 463/P/14 |
| 29 | VCPI 467/P/14 |
| 30 | VCPI 471a/P/14 |
| 31 | VCPI 478/P/14 |
| 32 | VCPI 518/P/14 |
| 33 | VCPI 550/P/14 |
| 34 | VCPI 714/P/14 |
| 35 | VCPI 717/P/14 |
| 36 | VCPI 1060/P/14 |
| 37 | VCPI 74/P/15 |
| 38 | VCPI 213/P/15 |

*Candida auris* antifungal susceptibility testing (AFST). Antifungal susceptibility testing was performed in duplicate for each strain in accordance with the guidelines described in CLSI documents M27-A3 (CLSI, 2008). *C. parapsilosis* ATCC 22019 and *C. krusei* ATCC 6258 were used as quality control strains. CD101, CAS, MICA, and FLU were obtained as standard powders from their manufacturer, and stock solutions were prepared by dissolving the compounds in water (CAS, MICA) or 100% dimethyl sulfoxide (DMSO) (CD101, FLU).

FKS1 HS1 PCR/sequencing. FKS1 HS1 PCR was carried out in the T100 thermal cycler (Bio-Rad) in a 30-µl reaction volume using EmeraldAmp MAX PCR Master Mix (Ta-KaRa). PCR mixtures contained 1 µl of each primer: Cspp_F2275 (5'-AATGGGCTGGTGCTCAACAT-3') and Cspp_R3070 (5'-CCTTCAATTTCAGATGGAACTT-GATG-3') at 10 µM. A sterile toothpick with a touch of testing single colony was dipped into the PCR reaction mastermix, and then FKS1 HS1 PCR were performed. The time-temperature profile included initial denaturation for 3 min at 94° C. followed by 35 cycles of 30 s at 94° C., 30 s at 53° C., and 90 s at 72° C. Amplicons were visualized on GelStar Nucleic Acid Gel Stain (Lonza) stained 1% agarose gel, purified by using ZR DNA Sequencing Clean-up Kit (Zymo Research), and sequenced by Genewiz. Sequencing results were analyzed by SeqMan Pro 14 (DNASTAR Lasergene).

Results

*Candida auris* antifungal susceptibility testing (AFST). The MIC (µg/ML) distributions of *C. auris* isolates for CD101, CAS, MICA, and FLU are shown in Table 11. All *C. auris* isolates (38) were resistant to fluconazole. Four (4) isolates were resistant to all tested echinocandins (CD101, CAS, MICA). CD101 exhibited activity similar to MICA.

FKS1 HS1 PCR/sequencing. Results of *C. auris* isolates FKS1 HS1 sequence analysis are shown in Table 11. Thirty four (34) echinocandin-sensitive isolates presented wild-type (WT) genotype within FKS1 HS1 region. Four (4) isolates (strain #s: 16, 25, 27, and 30 in Table 11), determined as echinocandin-resistant, exhibited serine to phenylalanine amino acid substitution in position equivalent to FKS1 HS1 S645 in *Candida albicans*.

TABLE 11

In vitro antifungal susceptibility profile and FKS1 HS1 characteristics of *Candida auris* strains

| | C. auris strain # | CD101 | | CAS | | MICA | | FLU | | |
|---|---|---|---|---|---|---|---|---|---|---|
| Strain # | (India) | 24 h | 48 h | 24 h | 48 h | 24 h | 48 h | 24 h | 48 h | FKS1 HS1 |
| 1 | VPCI 669/P/12 | 0.5 | 0.5 | 0.25* | >16** | 0.125 | 0.25 | >128 | >128 | WT |
| 2 | VCPI 671/P/12 | 0.5 | 0.5 | 0.25* | >16** | 0.125 | 0.25 | >128 | >128 | WT |
| 3 | VCPI 674/P/12 | 0.25 | 0.25 | 0.25* | 0.25* | 0.06 | 0.125 | >128 | 128 | WT |
| 4 | VCPI 683/P/12 | 0.5 | 0.5 | 0.25* | >16** | 0.125 | 0.25 | >128 | >128 | WT |
| 5 | VCPI 692/P/12 | 0.5 | 0.5 | 0.25* | >16** | 0.125 | 0.25 | >128 | >128 | WT |
| 6 | VCPI 712/P/12 | 0.25 | 0.25 | 0.25* | 0.25* | 0.125 | 0.125 | >128 | 128 | WT |
| 7 | VCPI 471/P/13 | 0.5 | 0.5 | 1* | >16** | 0.25 | 0.25 | >128 | >128 | WT |
| 8 | VCPI 475/P/13 | 0.5 | 0.5 | 0.25* | 0.25* | 0.125 | 0.25 | >128 | 64 | WT |
| 9 | VCPI 478/P/13 | 0.25 | 0.25 | 0.25* | >16** | 0.125 | 0.125 | >128 | 128 | WT |
| 10 | VCPI 479/P/13 | 0.25 | 0.25 | 0.5* | >16** | 0.125 | 0.125 | >128 | 128 | WT |

TABLE 11-continued

In vitro antifungal susceptibility profile and FKS1 HS1 characteristics of *Candida auris* strains

| Strain # | C. auris strain # (India) | CD101 24 h | CD101 48 h | CAS 24 h | CAS 48 h | MICA 24 h | MICA 48 h | FLU 24 h | FLU 48 h | FKS1 HS1 |
|---|---|---|---|---|---|---|---|---|---|---|
| 11 | VCPI 480/P/13 | 0.25 | 0.25 | 0.5* | >16** | 0.125 | 0.125 | >128 | >128 | WT |
| 12 | VCPI 482/P/13 | 0.25 | 0.25 | 0.5* | >16** | 0.125 | 0.125 | >128 | >128 | WT |
| 13 | VCPI 483/P/13 | 0.25 | 0.25 | 0.25* | 0.25* | 0.125 | 0.125 | >128 | 128 | WT |
| 14 | VCPI 1130/P/13 | 0.5 | 0.25 | 0.5* | 0.5* | 0.125 | 0.125 | 32 | 64 | WT |
| 15 | VCPI 1132/P/13 | 0.5 | 0.25 | 0.5* | 0.5* | 0.125 | 0.125 | 128 | 128 | WT |
| 16 | VCPI 1133/P/13 | 16 | >16 | 16 | >16 | 16 | >16 | >128 | >128 | S645F/S |
| 17 | VCPI 105/P/14 | 0.25 | 0.25 | 0.5* | 1* | 0.125 | 0.125 | 128 | 128 | WT |
| 18 | VCPI 107/P/14 | 0.125 | 0.125 | 0.25* | 0.5* | 0.06 | 0.06 | 64 | >128 | WT |
| 19 | VCPI 510/P/14 | 0.25 | 0.25 | 0.5* | >16** | 0.125 | 0.125 | >128 | >128 | WT |
| 20 | VCPI 511/P/14 | 0.25 | 0.25 | 0.5* | >16** | 0.125 | 0.125 | 128 | >128 | WT |
| 21 | VCPI 512/P/14 | 0.25 | 0.25 | 0.5* | 1* | 0.125 | 0.125 | 16 | >128 | WT |
| 22 | VCPI 513/P/14 | 0.5 | 0.5 | 1* | >16** | 0.125 | 0.25 | >128 | >128 | WT |
| 23 | VCPI 514/P/14 | 0.5 | 0.5 | 0.5* | 1* | 0.25 | 0.25 | >128 | >128 | WT |
| 24 | VCPI 250/P/14 | 0.25 | 0.25 | 0.5 | 0.5* | 0.125 | 0.125 | 64 | >128 | WT |
| 25 | VCPI 265/P/14 | 16 | >16 | 8 | >16 | 16 | >16 | >128 | >128 | S645F |
| 26 | VCPI 266/P/14 | 0.5 | 0.25 | 0.125* | 0.125* | 0.125 | 0.125 | >128 | >128 | WT |
| 27 | VCPI 462/P/14 | 16 | >16 | 8 | >16 | 16 | >16 | >128 | >128 | S645F |
| 28 | VCPI 463/P/14 | 0.125 | 0.125 | 0.5* | 0.5* | 0.125 | 0.125 | >128 | >128 | WT |
| 29 | VCPI 467/P/14 | 0.25 | 0.25 | 0.125* | 0.5* | 0.25 | 0.25 | >128 | >128 | WT |
| 30 | VCPI 471a/P/14 | 16 | >16 | 4 | >16 | 16 | >16 | >128 | >128 | S645F |
| 31 | VCPI 478/P/14 | 0.5 | 1 | 1* | 2* | 0.5 | 0.5 | >128 | >128 | WT |
| 32 | VCPI 518/P/14 | 0.5 | 0.5 | 0.5* | 16** | 0.25 | 0.5 | >128 | >128 | WT |
| 33 | VCPI 550/P/14 | 0.5 | 1 | 0.125* | 0.25* | 0.25 | 0.5 | >128 | >128 | WT |
| 34 | VCPI 714/P/14 | 0.25 | 0.25 | 0.5* | >16** | 0.125 | 0.25 | >128 | >128 | WT |
| 35 | VCPI 717/P/14 | 0.25 | 0.25 | 0.5* | >16** | 0.125 | 0.125 | 4 | >128 | WT |
| 36 | VCPI 1060/P/14 | 0.25 | 0.25 | 0.5* | >16** | 0.25 | 0.25 | >128 | >128 | WT |
| 37 | VCPI 74/P/15 | 0.25 | 0.25 | 0.5* | >16** | 0.25 | 0.25 | >128 | >128 | WT |
| 38 | VCPI 213/P/15 | 0.25 | 0.25 | 0.5* | >16** | 0.25 | 0.25 | >128 | >128 | WT |

(*CAS paradoxical effect -> 16 mg/L; **loss of CAS paradoxical effect, no possibility to read MIC, fungal growth reduction <50%)

Conclusions

High fluconazole resistance is common in clinical isolates of *C. auris*. Most *C. auris* strains are susceptible to echinocandins. However, most strains breakthrough on caspofungin at 48 h but not with CD101 or other echinocandins. Echinocandin resistance in these *C. auris* isolates was associated with amino acid substitution (serine into phenylalanine, position equivalent to *C. albicans* S645) within the FKS1 HS1 region.

Example 10

In Vivo Pharmacokinetic/Pharmacodynamic (PK/PD) Evaluation of CD101 Against *C. albicans* and *C. glabrata*

Methods

4 *C. albicans* and 3 *C. glabrata* strains were used. MICs were determined by CLSI standards. Single dose plasma PK was determined in groups of three mice after IP doses of 1, 4, 16, and 64 mg/kg. For treatment studies, mice were rendered neutropenic via administration of cyclophosphamide at days −4, −1, +2 and +4. Mice were infected with 6.3±0.1 CFU/ml (*C. albicans*) or 6.2±0.2 CFU/ml (*C. glabrata*) injected into the lateral tail vein. Treatment dose range was 0.016-64 mg/kg, given once by IP injection 2 h after infection. Experiment duration was 7 days at which point kidneys were aseptically harvested for CFU counts. The Emax Hill equation was used to model the dose-response data to PK/PD index AUC/MIC. The static and 1-log kill doses, as well as associated AUC/MIC values were determined for each isolate.

Results

CD101 MICs were 0.008-0.06 mg/L for *C. albicans* and 0.06-0.5 mg/L for *C. glabrata*. Single dose plasma PK parameter ranges include: Cmax 2.6-77 mg/L, $AUC_{0-\infty}$ 93-4046 mg*h/L, T1/2 28-41 h. Dose-dependent cidal activity was observed with a maximal kill of over 2 $\log_{10}$ CFU/kidney. Average 24 h AUC over 7 days was used to model AUC/MIC data and fit the treatment response data well with $R^2$ 0.70 for *C. albicans* and $R^2$ 0.86 for *C. glabrata*. The static dose (SD) and 1-log kill dose and associated AUC/MIC values are shown in Table 12.

TABLE 12

| | Strain | MIC (mg/L) | Static Dose (mg/kg) | Stasis Ave 24 h AUC/MIC | 1 log kill dose (mg/kg) | 1 log kill Ave 24 h AUC/MIC |
|---|---|---|---|---|---|---|
| *C. albicans* | K-1 | 0.008 | 2.52 | 3426 | 5.26 | 6435 |
| | 580 | 0.016 | 1.20 | 948 | 2.03 | 1429 |
| | 98-17 | 0.06 | 1.34 | 274 | 2.73 | 490 |
| | 98-210 | 0.016 | 1.06 | 868 | 2.28 | 1574 |
| *C. glabrata* | 10956 | 0.5 | 6.29 | 120 | 17.3 | 301 |
| | 5592 | 0.06 | 0.03 | 21.7 | 0.51 | 114 |
| | 35315 | 0.25 | 0.34 | 17.9 | 2.39 | 105 |

Conclusions

CD101 demonstrated in vivo potency in the neutropenic murine disseminated candidiasis model against select *C. albicans* and *C. glabrata* strains. Similar to studies with other echinocandins, AUC/MIC fit the exposure-response data well and *C. glabrata* targets were numerically lower than *C. albicans*. PK/PD targets identified in this study will be useful for clinical dosing regimen optimization of CD101 in the context of human pharmacokinetics and MIC distribution.

Other Embodiments

All publications, patents, and patent applications mentioned in this specification are herein incorporated by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims. Other embodiments are within the claims.

What is claimed is:

1. A method of treating invasive candidiasis in a subject, wherein the method consists of:
   (i) (a) intravenously administering a first dose comprising 400 mg of CD101 in salt or neutral form,
   (b) intravenously administering a second dose comprising 200 mg of CD101 in salt or neutral form, and
   (c) optionally intravenously administering a third dose comprising 200 mg of CD101 in salt or neutral form,
      wherein the first dose is administered on day 1, the second dose is administered on day 8, and the third dose, if administered, is administered on day 15; and
      wherein the CD101 is administered as an aqueous pharmaceutical composition over a time period of 30 to 180 minutes or
   (ii) (a) intravenously administering a first dose comprising 400 mg of CD101 in salt or neutral form,
   (b) intravenously administering a second dose comprising 400 mg of CD101 in salt or neutral form, and
   (c) optionally intravenously administering a third dose comprising 400 mg of CD101 in salt or neutral form,
      wherein the first dose is administered on day 1, the second dose is administered on day 8, and the third dose, if administered, is administered on day 15; and
      wherein the CD101 is administered as an aqueous pharmaceutical composition over a time period of 30 to 180 minutes.

2. The method of claim 1, wherein the third dose is administered if on day 15 mycological eradication and/or clinical cure is not achieved in the subject or if on day 15 the subject displays symptoms of a fungal infection.

3. The method of claim 1, wherein the CD101 salt is CD101 acetate.

4. The method of claim 1, wherein the invasive candidiasis is candidemia.

* * * * *